United States Patent
Grabowska et al.

(10) Patent No.: US 9,650,388 B2
(45) Date of Patent: May 16, 2017

(54) FORM 2 CRYSTALLINE POLYMORPH OF A SALT OF N-[1-6-(ETHYNYL-3-OXO-HEXAHYDRO-FURO[3,2-B]PYRROLE-4-CARBONYL)-3-METHYL-BUTYL]-4-[5-FLUORO-2-(4-METHYL-PIPERAZINYL) THIAZOL-4-YL]-BENZAMIDE USEFUL AS CYSTEINE PROTEASE INHIBITOR

(71) Applicant: MEDIVIR AB, Huddinge (SE)

(72) Inventors: Urszula Grabowska, Essex (GB); Lourdes Salvador Oden, Huddinge (SE); Victor M. Diaz Perez, Cambridge (GB); Andrew Carr, Cambridge (GB)

(73) Assignee: MEDIVIR AB, Stockholm (SE)

( * ) Notice: Subject to any disclaimer, the term of this patent is extended or adjusted under 35 U.S.C. 154(b) by 0 days.

(21) Appl. No.: 14/911,992

(22) PCT Filed: Aug. 13, 2014

(86) PCT No.: PCT/EP2014/067374
§ 371 (c)(1),
(2) Date: Feb. 12, 2016

(87) PCT Pub. No.: WO2015/022385
PCT Pub. Date: Feb. 19, 2015

(65) Prior Publication Data
US 2016/0194334 A1 Jul. 7, 2016

(30) Foreign Application Priority Data
Aug. 13, 2013 (GB) .................................. 1314503.2

(51) Int. Cl.
*C07D 491/048* (2006.01)
*A61K 31/496* (2006.01)
*A61K 9/00* (2006.01)
*A61K 45/06* (2006.01)

(52) U.S. Cl.
CPC ........ *C07D 491/048* (2013.01); *A61K 9/0019* (2013.01); *A61K 9/0053* (2013.01); *A61K 31/496* (2013.01); *A61K 45/06* (2013.01); *C07B 2200/13* (2013.01)

(58) Field of Classification Search
None
See application file for complete search history.

(56) References Cited

FOREIGN PATENT DOCUMENTS

WO 2010034788 A1 4/2010

OTHER PUBLICATIONS

Biskobing, Expert Opinion on Investigational Drugs, vol. 12, p. 611-621 (2003).*
Cai et al. Expert Opinion on Therapeutic Patents, vol. 15, p. 33-48 (2005).*
Delaisse et al. Clinica Chimica Acta vol. 29, p. 223-234 (2000).*
Skoumal et al. Arthritis Res. Ther. vol. 7, p. R65-R70 (2005).*
Caira M R, Crystalline Polymorphism of organic compounds, Topics in Current Chemistry, Springer, Berlin, DE, vol. 198, Jan. 1, 1998, pp. 165163-165208.
International Search Report, Sep. 19, 2014.

* cited by examiner

*Primary Examiner* — Emily Bernhardt
(74) *Attorney, Agent, or Firm* — Gorman IP Law, APC

(57) ABSTRACT

There is provided Form 2 crystalline polymorph consisting of N-[1-6-(ethynyl-3-oxo-hexahydro-furo[3,2-b]pyrrole-4-carbonyl)-3-methyl-butyl]-4-[5-fluoro-2-(4-methyl-piperazin-1-yl)thiazol-4-yl]-benzamide monohydrochloride and N-[1-6-(ethynyl-3-oxo-hexahydro-furo[3,2-b]pyrrole-4-carbonyl)-3-methyl-butyl]-4-[5-fluoro-2-(4-methyl-piperazin-1-yl)thiazol-4-yl]benzamide hydrate monohydrochloride, its use as a medicament and methods for its preparation.

24 Claims, 9 Drawing Sheets

FORM 2 CRYSTALLINE POLYMORPH OF A SALT OF N-[1-6-(ETHYNYL-3-OXO-HEXAHYDRO-FURO[3,2-B]PYRROLE-4-CARBONYL)-3-METHYL-BUTYL]-4-[5-FLUORO-2-(4-METHYL-PIPERAZINYL) THIAZOL-4-YL]-BENZAMIDE USEFUL AS CYSTEINE PROTEASE INHIBITOR

This application is the National Phase Under 35 USC §371 of PCT International Application No. PCT/EP2014/067374 filed on Aug. 13, 2014, which claims priority under 35 U.S.C. §119 on Patent Application No. 1314503.2 filed in the United Kingdom on Aug. 13, 2013, the entire contents of each of which are hereby incorporated by reference.

FIELD OF THE INVENTION

The present invention relates to a particular crystalline form of a novel salt of known cysteine protease inhibitor N-[1-6-(ethynyl-3-oxo-hexahydro-furo[3,2-b]pyrrole-4-carbonyl)-3-methyl-butyl]-4-[5-fluoro-2-(4-methyl-piperazin-1-yl)thiazol-4-yl]-benzamide. The present invention also relates to pharmaceutical formulations containing the crystalline form and to therapeutic uses thereof, particularly for the treatment of disorders mediated by cathepsin K.

BACKGROUND OF THE INVENTION

The papain superfamily of cysteine proteases is widely distributed in diverse species including mammals, invertebrates, protozoa, plants and bacteria. A number of mammalian cathepsin enzymes, including cathepsins B, F, H, K, L, O and S, have been ascribed to this superfamily, and inappropriate regulation of their activity has been implicated in a number of metabolic disorders including arthritis, muscular dystrophy, inflammation, glomerulonephritis and tumour invasion. Pathogenic cathepsin like enzymes include the bacterial gingipains, the malarial falcipains I, II, III et seq and cysteine proteases from *Pneumocystis carinii*, *Trypanosoma cruzei* and *brucei*, *Crithidia fusiculata*, *Schistosoma* spp.

The inappropriate regulation of cathepsin K has been implicated in a number of disorders including osteoporosis, gingival diseases such as gingivitis and periodontitis, Paget's disease, hypercalcaemia of malignancy and metastatic bone disease. In view of its elevated levels in chondroclasts of osteoarthritic synovium, cathepsin K is implicated in diseases characterised by excessive cartilage or matrix degradation, such as osteoarthritis and rheumatoid arthritis. Metastatic neoplastic cells typically express high levels of proteolytic enzymes that degrade the surrounding matrix. Also, such diseases are associated with high levels of bone turnover. Hence inhibition of cathepsin K may assist in preventing secondary metastases both by attenuating bone remodelling and the invasiveness of cancer cells.

International patent application WO2010/034788 discloses a number of cysteine protease inhibitors including N-[1-6-(ethynyl-3-oxo-hexahydro-furo[3,2-b]pyrrole-4-carbonyl)-3-methyl-butyl]-4-[5-fluoro-2-(4-methyl-piperazin-1-yl)thiazol-4-yl]-benzamide in the form of the free base which is disclosed therein as Example 2. This compound and its free base are referred to herein respectively as "Compound I" and "Compound I free base".

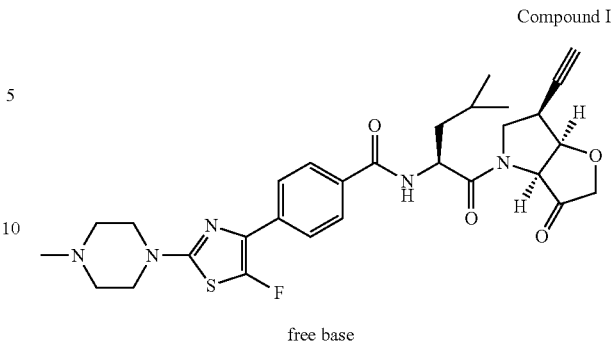

Compound I free base

It is acknowledged on page 3 of WO2010/034788 that cysteine protease inhibitors of that particular series could also exist in the form of a hydrate. In respect of its use as a pharmaceutical agent, Compound I free base suffers from a number of disadvantages relating to its relatively low water solubility and low thermal stability.

There is therefore a need for a form of Compound I which has one or more of the following properties:
(i) high water solubility
(ii) a high degree of crystallinity
(iii) good moisture stability
(iv) good thermal stability.

SUMMARY OF THE INVENTION

According to the present invention there is provided Form 2 crystalline polymorph consisting of N-[1-6-(ethynyl-3-oxo-hexahydro-furo[3,2-b]pyrrole-4-carbonyl)-3-methyl-butyl]-4-[5-fluoro-2-(4-methyl-piperazin-1-yl)thiazol-4-yl]-benzamide monohydrochloride and N-[1-6-(ethynyl-3-oxo-hexahydro-furo[3,2-b]pyrrole-4-carbonyl)-3-methyl-butyl]-4-[5-fluoro-2-(4-methyl-piperazin-1-yl)thiazol-4-yl]-benzamide hydrate monohydrochloride.

Form 2 crystalline polymorph has an improved physicochemical profile compared with Compound I free base, with other salt forms of Compound I and with other crystalline polymorph forms of N-[1-6-(ethynyl-3-oxo-hexahydro-furo[3,2-b]pyrrole-4-carbonyl)-3-methyl-butyl]-4-[5-fluoro-2-(4-methyl-piperazin-1-yl)thiazol-4-yl]-benzamide monohydrochloride (such as the Form 1 crystalline polymorph) and in particular is characterised by high crystallinity, good moisture stability, good thermal stability and high water solubility. Accordingly it has very favourable properties for the manufacture of a pharmaceutical product.

DETAILED DESCRIPTION OF THE INVENTION

Water solubility (i.e. hydrophilicity) is an important physical property of pharmaceutical agents which impacts their pharmacokinetics. In many circumstances an increased water solubility is desirable.

Crystallinity is another important physical property. Highly crystalline solids are generally easier to handle (for example, having more consistent physical properties) compared to amorphous or partially-crystalline solids. Furthermore, the exact crystalline form can affect, for example, dissolution rates and stability (such as moisture stability). Crystalline forms of solids often have low water solubility e.g. as compared with amorphous forms.

Consistency and reliability in pharmaceutical applications are of the utmost importance, both in the context of the initial manufacture of a pharmaceutical product and during the subsequent period prior to administration. Thus thermal stability and moisture stability are important physical properties of pharmaceutical agents because they impact on how the agents may be stored and handled. High thermal stability and moisture stability is desired to avoid chemical breakdown or change of physical form during processing steps (e.g. chemical synthesis, formulation, size reduction (if needed)) or during storage.

Form 2 crystalline polymorph exists as a single crystalline phase consisting of two components (A and B), as illustrated below.

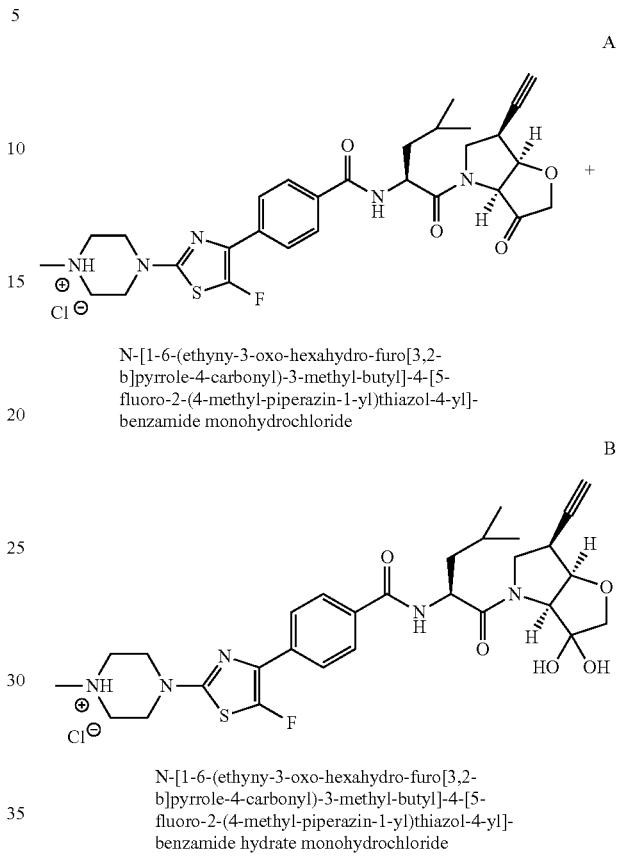

Figure 1:
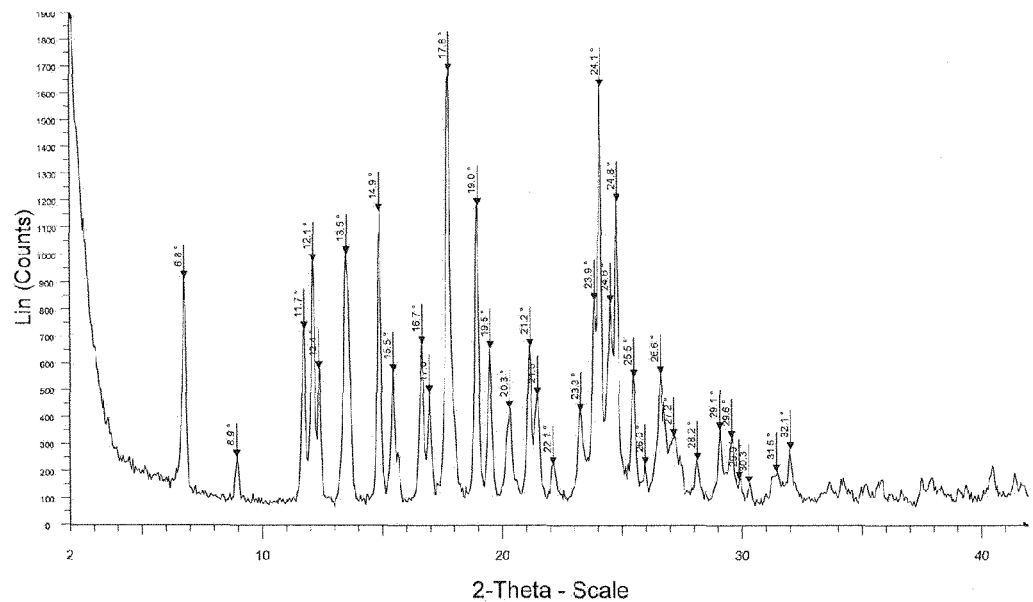
FIG. 1 shows an X-ray powder diffraction pattern of a sample of Form 2 crystalline polymorph.

N-[1-6-(ethyny-3-oxo-hexahydro-furo[3,2-b]pyrrole-4-carbonyl)-3-methyl-butyl]-4-[5-fluoro-2-(4-methyl-piperazin-1-yl)thiazol-4-yl]-benzamide monohydrochloride N-[1-6-(ethyny-3-oxo-hexahydro-furo[3,2-b]pyrrole-4-carbonyl)-3-methyl-butyl]-4-[5-fluoro-2-(4-methyl-piperazin-1-yl)thiazol-4-yl]-benzamide hydrate monohydrochloride Form 2 crystalline polymorph is characterised by having an X-ray powder diffraction pattern substantially as shown in FIG. 1.

Thus, the present invention provides Form 2 crystalline polymorph consisting of N-[1-6-(ethynyl-3-oxo-hexahydro-furo[3,2-b]pyrrole-4-carbonyl)-3-methyl-butyl]-4-[5-fluoro-2-(4-methyl-piperazin-1-yl)thiazol-4-yl]-benzamide monohydrochloride and N-[1-6-(ethynyl-3-oxo-hexahydro-furo[3,2-b]pyrrole-4-carbonyl)-3-methyl-butyl]-4-[5-fluoro-2-(4-methyl-piperazin-1-yl)thiazol-4-yl]-benzamide hydrate monohydrochloride, having an X-ray powder diffraction pattern substantially as shown in FIG. 1.

For example, this pattern has major peaks at positions 6.8, 12.4, 14.9, 16.7, 17.0, 17.8, 24.1, 24.6, 24.8, 27.2, 28.2, 32.1 (±0.2 degrees, 2-theta values), several of these signals being characteristic of the Form 2 crystalline polymorph.

Thus, the present invention provides Form 2 crystalline polymorph consisting of N-[1-6-(ethynyl-3-oxo-hexahydro-furo[3,2-b]pyrrole-4-carbonyl)-3-methyl-butyl]-4-[5-fluoro-2-(4-methyl-piperazin-1-yl)thiazol-4-yl]-benzamide monohydrochloride and N-[1-6-(ethynyl-3-oxo-hexahydro-furo[3,2-b]pyrrole-4-carbonyl)-3-methyl-butyl]-4-[5-fluoro-2-(4-methyl-piperazin-1-yl)thiazol-4-yl]-benzamide hydrate monohydrochloride, having an X-ray powder diffraction pattern with at least three (for example, three, four, five, six, seven, eight, nine, ten, eleven or all twelve) signals at 6.8, 12.4, 14.9, 16.7, 17.0, 17.8, 24.1, 24.6, 24.8, 27.2, 28.2, 32.1 (±0.2 degrees, 2-theta values).

The signals at 6.8, 12.4, 14.9, 16.7, 17.8, 24.1, 24.6 and 24.8 have comparatively high relative intensity (more than 30%—see FIG. 1) and therefore it is preferred to see at least three (for example three, four, five, six, seven or all eight) of these peaks. The signals at 6.8, 14.9, 17.8, 24.1, 24.6 and 24.8 have particularly high relative intensity (more than 40%—see FIG. 1) and therefore it is preferred to see at least three (for example three, four, five or all six) of these peaks.

The signals at 13.5, 19.0 and 23.9 (±0.2 degrees, 2-theta values) also have particularly high relative intensity (more than 40%—see FIG. 1) and therefore it is preferred to see all three of these peaks.

Figure 17:
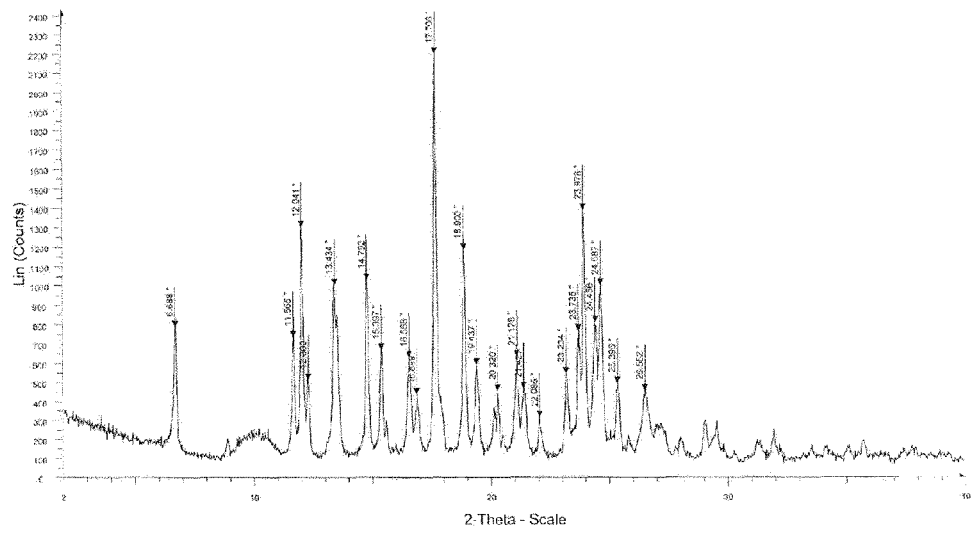
FIG. 17 shows an X-ray powder diffraction pattern of a sample of Form 2 crystalline polymorph obtained using the large scale procedure of Example 17.

Form 2 crystalline polymorph prepared on a large scale according to Example 17 has an X-ray powder diffraction pattern substantially as shown in FIG. 17, which is in good agreement with the pattern shown in FIG. 1.

Figure 2:
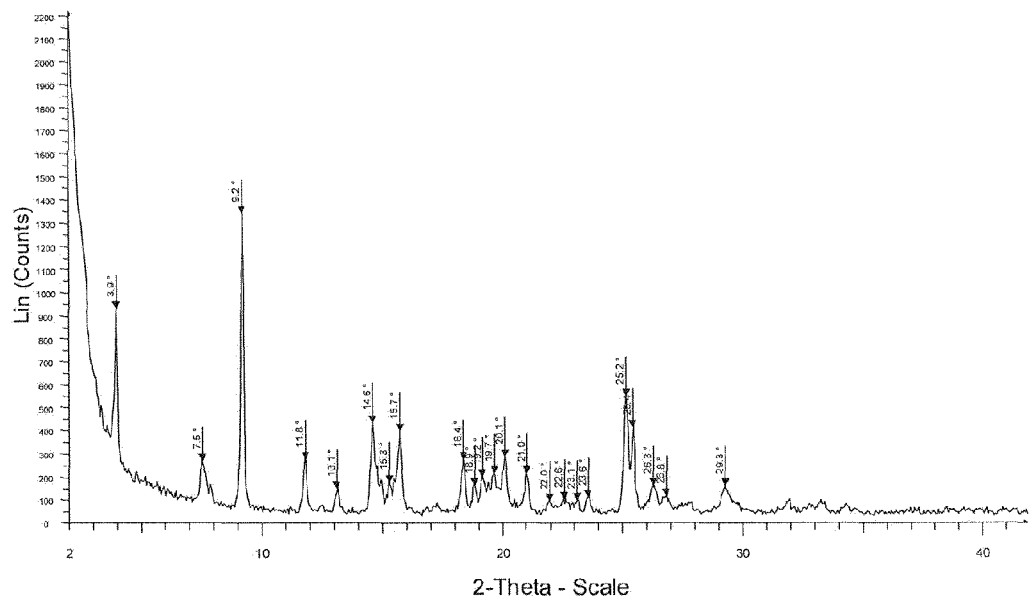
FIG. 2 shows an X-ray powder diffraction pattern of a sample of the crystalline polymorph form of N-[1-6-(ethynyl-3-oxo-hexahydro-furo[3,2-b]pyrrole-4-carbonyl)-3-methyl-butyl]-4-[5-fluoro-2-(4-methyl-piperazin-1-yl)thiazol-4-yl]-benzamide monohydrochloride known as the Form 1 crystalline polymorph.

Suitably Form 2 crystalline polymorph has an X-ray powder diffraction pattern which does not have signals having relative intensity of 10% or more at 3.9, 7.5 and 9.2 (±0.2 degrees, 2-theta values) which appear in the spectrum of the Form 1 crystalline polymorph (see FIG. 2).

Form 2 crystalline polymorph crystallises in an orthorhombic crystal system, and is characterised by having a $P2_12_12_1$ space group at a temperature of about 294 K and/or unit cell dimensions of a=7.5 Å, b=15.3 Å, c=26.3 Å at a temperature of about 294 K.

Thus, the present invention provides Form 2 crystalline polymorph consisting of N-[1-6-(ethynyl-3-oxo-hexahydro-furo[3,2-b]pyrrole-4-carbonyl)-3-methyl-butyl]-4-[5-fluoro-2-(4-methyl-piperazin-1-yl)thiazol-4-yl]-benzamide monohydrochloride and N-[1-6-(ethynyl-3-oxo-hexahydro-furo[3,2-b]pyrrole-4-carbonyl)-3-methyl-butyl]-4-[5-fluoro-2-(4-methyl-piperazin-1-yl)thiazol-4-yl]-benzamide hydrate monohydrochloride, wherein Form 2 crystalline polymorph is characterized by having a $P2_12_12_1$ space group at a temperature of about 294 K and/or unit cell dimensions of a=7.5 Å, b=15.3 Å, c=26.3 Å at a temperature of about 294 K.

Despite the fact that Form 2 crystalline polymorph consists of two different chemical entities (ketone and hydrate forms of compound I monohydrochloride) the Form 2 polymorph exists as a single crystalline phase. Within the single crystalline phase, the proportion of ketone form (A) in the crystal may be greater than the proportion of hydrate form (B). In one embodiment, the molar ratio of ketone form to hydrate form is from about 1:1 to about 4:1, for example from about 1.2:1 to about 3:1, such as about 50:50, 51:49, :52:48, 53:47, 54:46, 55:45, 56:44, 57:43, 58:42, 59:41, 60:40, 61:39, 62:38, 63:37, 64:36, 65:35, 66:34, 67:33, 68:32, 69:31, 70:30, 71:29, 72:28, 73:27, 74:26, 75:25, 76:24, 77:23, 78:22, 79:21 or 80:20. In another embodiment, the molar ratio of ketone form to hydrate form is from about 4:1 to about 5:1 for example 80:20, 81:19, 82:18, 83:17 or 84:16.

Thus, in one aspect the present invention provides Form 2 crystalline polymorph consisting of N-[1-6-(ethynyl-3-oxo-hexahydro-furo[3,2-b]pyrrole-4-carbonyl)-3-methyl-butyl]-4-[5-fluoro-2-(4-methyl-piperazin-1-yl)thiazol-4-yl]-benzamide monohydrochloride and N-[1-6-(ethynyl-3-oxo-hexahydro-furo[3,2-b]pyrrole-4-carbonyl)-3-methyl-butyl]-4-[5-fluoro-2-(4-methyl-piperazin-1-yl)thiazol-4-yl]-benzamide hydrate monohydrochloride, wherein the molar ratio of N-[1-6-(ethynyl-3-oxo-hexahydro-furo[3,2-b]pyrrole-4-carbonyl)-3-methyl-butyl]-4-[5-fluoro-2-(4-methyl-piperazin-1-yl)thiazol-4-yl]-benzamide monohydrochloride to N-[1-6-(ethynyl-3-oxo-hexahydro-furo[3,2-b]pyrrole-4-carbonyl)-3-methyl-butyl]-4-[5-fluoro-2-(4-methyl-piperazin-1-yl)thiazol-4-yl]-benzamide hydrate monohydrochloride is from about 1:1 to about 4:1, for example from about 1.2:1 to about 3:1, such as about 50:50, 51:49, :52:48, 53:47, 54:46, 55:45, 56:44, 57:43, 58:42, 59:41, 60:40, 61:39, 62:38, 63:37, 64:36, 65:35, 66:34, 67:33, 68:32, 69:31, 70:30, 71:29, 72:28, 73:27, 74:26, 75:25, 76:24, 77:23, 78:22, 79:21 or 80:20. In another aspect the present invention provides Form 2 crystalline polymorph consisting of N-[1-6-(ethynyl-3-oxo-hexahydro-furo[3,2-b]pyrrole-4-carbonyl)-3-methyl-butyl]-4-[5-fluoro-2-(4-methyl-piperazin-1-yl)thiazol-4-yl]-benzamide monohydrochloride and N-[1-6-(ethynyl-3-oxo-hexahydro-furo[3,2-b]pyrrole-4-carbonyl)-3-methyl-butyl]-4-[5-fluoro-2-(4-methyl-piperazin-1-yl)thiazol-4-yl]-benzamide hydrate monohydrochloride, wherein the molar ratio of N-[1-6-(ethynyl-3-oxo-hexahydro-furo[3,2-b]pyrrole-4-carbonyl)-3-methyl-butyl]-4-[5-fluoro-2-(4-methyl-piperazin-1-yl)thiazol-4-yl]-benzamide monohydrochloride to N-[1-6-(ethynyl-3-oxo-hexahydro-furo[3,2-b]pyrrole-4-carbonyl)-3-methyl-butyl]-4-[5-fluoro-2-(4-methyl-piperazin-1-yl)thiazol-4-yl]-benzamide hydrate monohydrochloride is from about 4:1 to about 5:1, such as 80:20, 81:19, 82:18, 83:17 or 84:16.

The ratio of ketone to hydrate form may be determined by $^{13}C$ NMR or $^1H$ NMR analysis, preferably by solid state $^{13}C$ NMR analysis. Form 2 crystalline polymorph prepared according to Example 5 was determined to have a ketone:hydrate ratio of 67:33 (determined by solid state $^{13}C$ NMR analysis, see Example 11). Form 2 crystalline polymorph prepared according to Example 17 was determined to have a ketone:hydrate ratio of 82:18 (determined by $^1H$ NMR analysis). However, in cases where the Form 2 crystalline polymorph prepared via different methods was determined to have different ketone:hydrate ratios, the X-ray diffraction patterns obtained on samples of the material were substantially the same, indicating that the exact ratio of ketone:hydrate in the Form 2 polymorph is not a key characterising feature of the material.

As discussed in more detail in the Examples, the present inventors have identified another crystalline polymorph form of N-[1-6-(ethynyl-3-oxo-hexahydro-furo[3,2-b]pyrrole-4-carbonyl)-3-methyl-butyl]-4-[5-fluoro-2-(4-methyl-piperazin-1-yl)thiazol-4-yl]-benzamide monohydrochloride, which may be prepared according to one of the methods described in Example 8. This form, referred to herein as "the Form 1 crystalline polymorph" has an X-ray powder diffraction pattern substantially as shown in FIG. 2. The ratio of ketone to hydrate in the Form 1 crystalline polymorph was not determined. The Form 1 crystalline polymorph has far less attractive properties than Form 2 crystalline polymorph, being less thermally stable and less water soluble, and does not form an aspect of the invention.

It should be noted that the nomenclature of the compounds described herein may vary. Compound I free base is described herein as N-[1-6-(ethynyl-3-oxo-hexahydro-furo[3,2-b]pyrrole-4-carbonyl)-3-methyl-butyl]-4-[5-fluoro-2-(4-methyl-piperazin-1-yl)thiazol-4-yl]-benzamide, but may also be referred to as N—((S)-1-((3aS,6R,6aR)-6-ethynyl-3-oxotetrahydro-2H-furo[3,2-b]pyrrol-4(5H)-yl)-4-methyl-1-oxopentan-2-yl)-4-(5-fluoro-2-(4-methylpiperazin-1-yl)thiazol-4-yl)benzamide. For the avoidance of doubt, both compound names refer to the same chemical structure of:

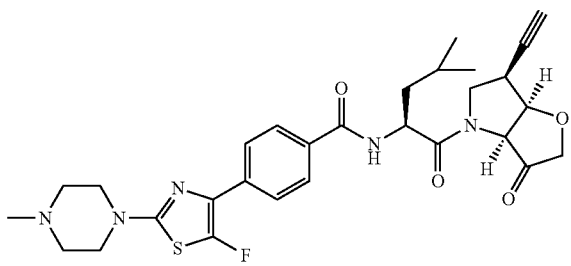 [SMILES: C#C[C@@H]1CN(C(=O)[C@H](CC(C)C)NC(=O)c2ccc(-c3nc(N4CCN(C)CC4)sc3F)cc2)[C@@H]2C(=O)CO[C@H]12]

The divergence in the compound naming arises due to there being two different conventions for naming the following bicyclic unit:

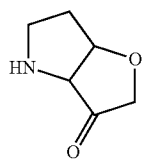

The unit may be referred to as "3-oxo-hexahydro-furo[3,2-b]pyrrole" or "3-oxotetrahydro-2H-furo[3,2-b]pyrrole". For the avoidance of doubt, both names refer to the same structure.

Figure 3:
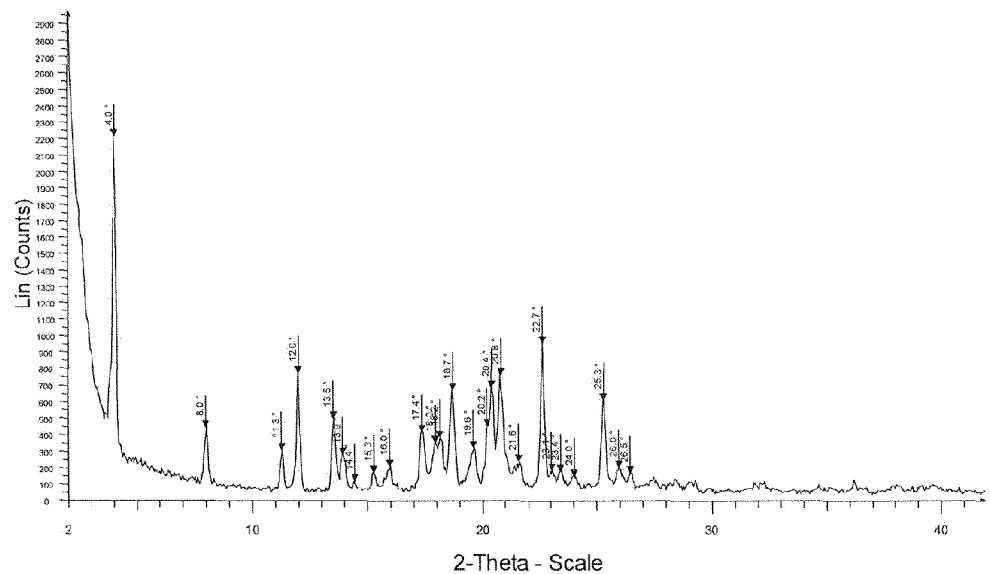
FIG. 3 shows an X-ray powder diffraction pattern of a sample of the crystalline form of Compound I free base.

Suitably Form 2 crystalline polymorph has an X-ray powder diffraction pattern which does not have signals having relative intensity of 10% or more at 4.0, 8.0, 20.8 and 22.7 (±0.2 degrees, 2-theta values) which appear in the spectrum of a form of the crystalline free base (see FIG. 3). The disadvantages of Compound I free base have already been mentioned, and include low water solubility and low thermal stability.

The term "relative intensity" will be understood to mean the intensity given as a percentage as the intensity of the signal of highest intensity in the spectrum, as illustrated by FIGS. 1 to 3.

Form 2 crystalline polymorph is unusual in structure in that it consists of two chemical entities—a ketone and a hydrate within the same crystalline phase in a ratio of about 1:1 to about 4:1 or to about 5:1, for example a ratio of 2:1 or 82:18. As described in Example 11 and illustrated in FIGS. 5-8, surprisingly, the ratio of ketone to hydrate did not change when samples of Form 2 crystalline polymorph were stored at different relative humidities. Furthermore, additional solid phase NMR experiments to determine the relaxation dependence of the spectra provided no evidence that the ketone and hydrate forms were in different phases (Example 11 and FIGS. 9 and 10). Hygroscopicity analysis using gravimetric vapour sorption (Example 15) confirmed the surprising findings of the solid state NMR experiments (Example 11), that the crystalline form was not at risk of humidity mediated change. Form 2 crystalline polymorph was also found to have significantly greater thermal stability compared to the crystalline free base and the Form 1 crystalline polymorph, as well as very high solubility.

Compound I free base may be prepared by the method taught in WO2010/034788 (the contents of which are herein incorporated by reference in their entirety)—see Example 1.

A method which is particularly suitable for preparing Compound I free base on a large scale is described in Example 16.

N-[1-6-(ethynyl-3-oxo-hexahydro-furo[3,2-b]pyrrole-4-carbonyl)-3-methyl-butyl]-4-[5-fluoro-2-(4-methyl-piperazin-1-yl)thiazol-4-yl]-benzamide monohydrochloride (the monohydrochloride salt of Compound I free base) may be prepared by the reaction of Compound I free base with hydrochloric acid.

Various methods for preparing Form 2 crystalline polymorph have been determined, including:

(a) crystallisation from solution in acetone, particularly with slow cooling (e.g. cooling from 50° C. to 20° C. at 0.1° C./min);

(b) crystallisation from solution in IPA, particularly with temperature cycling. A suitable temperature cycle involves cycling between 50° C. and 0° C. with 1 h ramps;

(c) crystallisation from solution in acetone, IPAc, EtOAc or MEK, particularly with temperature cycling. A suitable temperature cycle involves cycling between 50° C. and 20° C. with 1 h ramps.

Thus, a method for the preparation of Form 2 crystalline polymorph comprises reacting N-[1-6-(ethynyl-3-oxo-hexahydro-furo[3,2-b]pyrrole-4-carbonyl)-3-methyl-butyl]-4-[5-fluoro-2-(4-methyl-piperazin-1-yl)thiazol-4-yl]-benzamide free base with hydrochloric acid in the presence of a solvent selected from acetone, IPA, IPAc EtOAc, THF and MEK (especially acetone) and crystallizing the crystalline form from the said solvent. Crystallizing may be performed under conditions of slow cooling or temperature cycling.

In some embodiments it may be preferred to produce Form 2 crystalline polymorph by a process comprising crystallizing the Form 2 crystalline polymorph from a solution of N-[1-6-(ethynyl-3-oxo-hexahydro-furo[3,2-b]pyrrole-4-carbonyl)-3-methyl-butyl]-4-[5-fluoro-2-(4-methyl-piperazin-1-yl)thiazol-4-yl]-benzamide monohydrochloride in a solvent (e.g. one mentioned above) in the presence of a seed quantity of Form 2 crystalline polymorph.

An alternative example process involves seeding a solution of Compound I free base in acetone with a small quantity of Form 2 crystalline polymorph and adding a solution of hydrochloric acid in acetone. A suitable temperature for the reaction of Compound I free base with HCl is around 50° C., with subsequent cooling to 5° C. at 0.1° C./min to promote crystallisation.

Crystallisation may be promoted by use of antisolvent, e.g. TBME.

Thus another example process for preparation of the Form 2 crystalline polymorph involves crystallisation from a solution of IPA, THF or acetone using TBME as antisolvent.

In particular, such a process may involve first forming N-[1-6-(ethynyl-3-oxo-hexahydro-furo[3,2-b]pyrrole-4-carbonyl)-3-methyl-butyl]-4-[5-fluoro-2-(4-methyl-piperazin-1-yl)thiazol-4-yl]-benzamide monohydrochloride by treating a solution of Compound I free base in acetone with HCl in acetone, seeding with a small quantity of Form 2 crystalline polymorph and adding TBME as anti-solvent. These steps are typically performed at around 50° C. followed by cooling (say to 12° C.).

Thus, in one embodiment, there is provided Form 2 crystalline polymorph obtained when recrystallised from acetone with slow cooling (e.g. cooling from 50° C. to 20° C. at 0.1° C./min).

A process which is particularly suitable for preparing the Form 2 crystalline polymorph on a large scale (as described in detail in Example 17) involves rapidly heating a solution of Compound I free base in acetone, TBME and HCl to 50° C. The solution is then seeded with a small quantity of Form 2 crystalline polymorph which induces precipitation of the Form 2 crystalline polymorph, which is further induced by the addition of acetone and TBME as antisolvents. The resulting suspension is then rapidly cooled to 10° C.

Thus, in one embodiment, the present invention provides a method for the preparation of Form 2 crystalline polymorph comprising:
(i) reacting N-[1-6-(ethynyl-3-oxo-hexahydro-furo[3,2-b]pyrrole-4-carbonyl)-3-methyl-butyl]-4-[5-fluoro-2-(4-methyl-piperazin-1-yl)thiazol-4-yl]-benzamide free base with hydrochloric acid in the presence of acetone and TBME;
(ii) seeding the solution with Form 2 crystalline polymorph; and
(iii) inducing crystallization by the addition of acetone and TBME.

The above mentioned processes yield Form 2 crystalline polymorph. Thus, in one embodiment, there is provided Form 2 crystalline polymorph obtainable by a method described above.

As noted above, N-[1-6-(ethynyl-3-oxo-hexahydro-furo[3,2-b]pyrrole-4-carbonyl)-3-methyl-butyl]-4-[5-fluoro-2-(4-methyl-piperazin-1-yl)thiazol-4-yl]-benzamide monohydrochloride exists in certain less favoured polymorph forms which may be prepared by the following methods:

N-[1-6-(ethynyl-3-oxo-hexahydro-furo[3,2-b]pyrrole-4-carbonyl)-3-methyl-butyl]-4-[5-fluoro-2-(4-methyl-piperazin-1-yl)thiazol-4-yl]-benzamide monohydrochloride in amorphous form may be prepared by treatment of a solution of Compound I free base in IPAc with a solution of hydrochloric acid in dioxane at RT.

N-[1-6-(ethynyl-3-oxo-hexahydro-furo[3,2-b]pyrrole-4-carbonyl)-3-methyl-butyl]-4-[5-fluoro-2-(4-methyl-piperazin-1-yl)thiazol-4-yl]-benzamide monohydrochloride in crystalline Form 1 polymorph may be prepared by crystallisation by cooling from hot THF (e.g. at 50° C.) (e.g. 4 vol) in the presence of water (1% v/v) with cooling.

Accordingly, conditions which yield these other undesired forms should be avoided in the preparation of Form 2 crystalline polymorph.

Form 2 crystalline polymorph may be expected to be of use in the treatment of disorders mediated by cathepsin K.

In another aspect of the invention there is provided the use of Form 2 crystalline polymorph as a medicament. Also provided is the use of Form 2 crystalline polymorph in the manufacture of a medicament for the treatment of disorders mediated by cathepsin K. Additionally provided is a method for the treatment of a disorder mediated by cathepsin K comprising administering a safe and effective amount of Form 2 crystalline polymorph.

In one embodiment, an appropriate dosage level for Form 2 crystalline polymorph is in the order of 0.01-100 uM, such as 0.01-10 uM or 0.1-25 uM.

Particular disorders which may be mediated by cathepsin K include:
osteoporosis;
gingival diseases such as gingivitis and periodontitis;
Paget's disease;
hypercalcaemia of malignancy;
metastatic bone disease, for example bone cancer including neoplasia;
diseases characterised by excessive cartilage or matrix degradation, such as osteoarthritis and rheumatoid arthritis; and
pain.

The disorders of osteoporosis, metastatic bone disease such as bone cancer, osteoarthritis, and rheumatoid arthritis, especially osteoporosis or osteoarthritis, are of particular interest.

Thus, in one embodiment, the disorder mediated by cathepsin K is osteoporosis. In another embodiment, the disorder mediated by cathepsin K is metastatic bone disease, for example bone cancer including neoplasia. In another embodiment, the disorder mediated by cathepsin K is osteoarthritis. In another embodiment, the disorder mediated by cathepsin K is rheumatoid arthritis.

While it is possible for Form 2 crystalline polymorph to be administered in isolation, it will typically be presented as part of a pharmaceutical composition. Such a composition will comprise Form 2 crystalline polymorph together with one or more pharmaceutically acceptable excipients. Said pharmaceutically acceptable excipients will be suitable for administration and will be compatible with the other ingredients of the composition.

An additional aspect of the present invention is therefore a pharmaceutical composition comprising Form 2 crystalline polymorph and one or more pharmaceutically acceptable diluents or carriers.

The compositions include those suitable for oral, rectal, nasal, topical (including buccal and sublingual), vaginal or parenteral (including subcutaneous, intramuscular, intravenous and intradermal) administration. Suitably the pharmaceutical composition is an orally administered formulation. The compositions may conveniently be presented in unit dosage form (e.g. tablets and sustained release capsules) and may be prepared by any method known in the art of pharmacy.

Such methods include the step of bringing into association Form 2 crystalline polymorph with the one or more pharmaceutically acceptable diluents or carriers. In general, the compositions are prepared by uniformly and intimately bringing into association Form 2 crystalline polymorph with liquid carriers or finely divided solid carriers or both, and then if necessary shaping the product.

In a further aspect there is provided a method for the preparation of a pharmaceutical composition comprising bringing Form 2 crystalline polymorph into association with one or more pharmaceutically acceptable diluents or carriers.

Suitably, a single dose (of the pharmaceutical composition comprising Form 2 crystalline polymorph) will comprise about 25-200 mg of Form 2 crystalline polymorph, depending on intended indication and dosing regime, such as about 50-100 mg or 75-125 mg. For the osteoporosis indication a dosage unit of around 100 mg is generally convenient for a QD dosing regime. In one embodiment, the pharmaceutical composition comprises Form 2 crystalline polymorph and one or more pharmaceutically acceptable diluents or carriers in a ratio (weight/weight) of between about 1:2 and 1:100, such as between about 1:2 and 1:50, between about 1:2 and 1:20 or between about 1:3 and 1:10. (Form 2 crystalline polymorph:one or more pharmaceutically acceptable diluents or carriers).

The dosing regime for products comprising the Form 2 crystalline polymorph will generally be selected by the physician to take into account conventional factors of patient status and intended indication. Conventional BID and TID are envisaged. However, the DMPK (drug metabolism and pharmacokinetics) of the Form 2 crystalline polymorph and compound I are amenable to a QD dosage regime, which is advantageous, not only from a patient compliance viewpoint, but also because single daily dosing allows a diurnal PTH spike to occur, thereby facilitating anabolic bone growth. Accordingly an aspect of the invention provides a dosage unit adapted for QD administration, and suitable for indications such as osteoporosis, such as a dosage unit containing around 100 mg of the Form 2 crystalline polymorph and one or more pharmaceutically acceptable carriers or excipients.

Formulations for oral administration in the present invention may be presented as discrete units such as capsules, cachets or tablets each containing a predetermined amount of the active agent; as a powder or granules; as a solution or a suspension of the active agent in an aqueous liquid or a non-aqueous liquid; or as an oil-in-water liquid emulsion or a water in oil liquid emulsion and as a bolus etc.

With regard to compositions for oral administration (e.g. tablets and capsules), the term excipient includes: binding agents, for example syrup, acacia, gelatin, sorbitol, tragacanth, polyvinylpyrrolidone (Povidone), methylcellulose, ethylcellulose, sodium carboxymethylcellulose, hydroxypropylmethylcellulose, sucrose and starch; fillers and carriers, for example corn starch, gelatin, lactose, sucrose, microcrystalline cellulose, kaolin, mannitol, dicalcium phosphate, sodium chloride and alginic acid; and lubricants such as magnesium stearate, sodium stearate and other metallic stearates, glycerol stearate stearic acid, silicone fluid, talc waxes, oils and colloidal silica. Flavouring agents such as peppermint, oil of wintergreen, cherry flavouring or the like can also be used. It may be desirable to add a colouring agent to make the dosage form readily identifiable. Tablets may also be coated by methods well known in the art.

A tablet may be made by compression or moulding, optionally with one or more accessory ingredients. Compressed tablets may be prepared by compressing in a suitable machine the Form 2 crystalline polymorph in a free flowing form such as a powder or granules, optionally mixed with a binder, lubricant, inert diluent, preservative, surface-active or dispersing agent. Moulded tablets may be made by moulding in a suitable machine a mixture of the powdered compound moistened with an inert liquid diluent. The tablets may be optionally be coated or scored and may be formulated so as to provide slow or controlled release of the active agent.

Other formulations suitable for oral administration include lozenges comprising Form 2 crystalline polymorph in a flavoured base, usually sucrose and acacia or tragacanth; pastilles comprising the Form 2 crystalline polymorph in an inert base such as gelatin and glycerin, or sucrose and acacia; and mouthwashes comprising Form 2 crystalline polymorph in a suitable liquid carrier.

Appropriate dosage levels for Form 2 crystalline polymorph will depend upon the indication and the individual patient receiving treatment. Suitable dosages may be determined by conventional animal trials. Dosages providing intracellular (for inhibition of physiological proteases of the papain superfamily) concentrations of the order 0.01-100 uM, such as 0.01-10 uM or 0.1-25 uM, are typically desirable and achievable.

When used as a medicament, it may be advantageous for Form 2 crystalline polymorph to be administered in combination with one or more further pharmaceutically active agents. Such further pharmaceutically active agents will be selected appropriately depending on the disorder to be treated. Form 2 crystalline polymorph and a further pharmaceutically active agent may be administered concurrently, sequentially or at different times through the same or different routes.

Where appropriate administration regimes are possible, Form 2 crystalline polymorph and a further pharmaceutically active agent may be formulated together in a pharmaceutical combination.

Form 2 crystalline polymorph is, for example, useful in combination with known agents useful for treating or preventing osteoporosis, glucocorticoid induced osteoporosis, Paget's disease, abnormally increased bone turnover, periodontal disease, tooth loss, bone fractures, atherosclerosis, obesity, parasitic infection, rheumatoid arthritis, osteoarthritis, periprosthetic osteolysis, osteogenesis imperfecta, metastatic bone disease, hypercalcemia of malignancy, and multiple myeloma. Combinations of Form 2 crystalline polymorph with other agents useful in treating or preventing osteoporosis or other bone disorders are therefore considered to fall within the scope of the invention.

A person of ordinary skill in the art would be able to discern which combinations of agents would be useful based on the particular characteristics of the drugs and the disease involved. Such agents include the following: an organic bisphosphonate; an estrogen receptor modulator; an androgen receptor modulator; an inhibitor of osteoclast proton ATPase; an inhibitor of HMG-CoA reductase; an integrin receptor antagonist; Vitamin D or an analogue thereof, an osteoblast anabolic agent, such as PTH; a selective cyclooxygenase-2 inhibitor (COX-2 inhibitor); an inhibitor of interleukin-1-beta; a LOX/COX inhibitor, a RANKL inhibitor; an anti-sclerostin antibody and pharmaceutically acceptable salts and mixtures thereof.

"Androgen receptor modulators" refers to compounds which interfere or inhibit the binding of androgens to the receptor, regardless of mechanism. Examples of androgen receptor modulators include finasteride and other 5 cc-reductase inhibitors, nilutamide, flutamide, bicalutamide, liarozole, and abiraterone acetate.

"An inhibitor of osteoclast proton ATPase" refers to an inhibitor of the proton ATPase, which is found on the apical membrane of the osteoclast, and has been reported to play a significant role in the bone resorption process. This proton pump represents an attractive target for the design of inhibitors of bone resorption which are potentially useful for the treatment and prevention of osteoporosis and related metabolic diseases. See C. Farina et al., "Selective inhibitors of the osteoclast vacuolar proton ATPase as novel bone anti-resorptive agents," DDT, 4: 163-172 (1999), which is hereby incorporated by reference in its entirety.

"HMG-CoA reductase inhibitors" refers to inhibitors of 3-hydroxy-3-methylglutaryl CoA reductase. Compounds which have inhibitory activity for HMG-CoA reductase can be readily identified by using assays well-known in the art. For example, see the assays described or cited in U.S. Pat. No. 4,231,938 at col 6, and WO 84/02131 at pp. 30-33. The terms "HMG-CoA reductase inhibitor" and "inhibitor of IG-CoA reductase" have the same meaning when used herein.

Examples of HMG-CoA reductase inhibitors that may be used include but are not limited to lovastatin (MEVACOR; see U.S. Pat. Nos. 4,231,938, 4,294,926 and 4,319,039), simvastatin—19 (ZOCOR); see U.S. Pat. Nos. 4,444,784, 4,820,850 and 4,916,239), pravastatin (PRAVACHOL; see U.S. Pat. Nos. 4,346,227, 4,537,859, 4,410,629, 5,030,447 and 5,180,589), fluvastatin (LESCOL); see U.S. Pat. Nos. 5,354,772, 4,911,165, 4,929,437, 5,189,164, 5,118,853, 5,290,946 and 5,356,896), atorvastatin (LIPITOR; see U.S. Pat. Nos. 5,273,995, 4,681,893, 5,489,691 and 5,342,952) and cerivastatin (also known as rivastatin and BAYCHOL; see U.S. Pat. No. 5,177,080). The structural formulae of these and additional HMG-CoA reductase inhibitors that may be used in the instant methods are described at page 87 of M. Yalpani, "Cholesterol Lowering Drugs", Chemistry & Industry, pp. 85-89 (5 Feb. 1996) and U.S. Pat. Nos.

4,782,084 and 4,885,314. The term HMG-CoA reductase inhibitor as used herein includes all pharmaceutically acceptable lactone and open-acid forms (i.e., where the lactone ring is opened to form the free acid) as well as salt and ester forms of compounds which have HMG-CoA reductase inhibitory activity, and therefore the use of such salts, esters, open-acid and lactone forms is included within the scope of this invention.

In HMG-CoA reductase inhibitors where an open-acid form can exist, salt and ester forms may preferably be formed from the open-acid, and all such forms are included within the meaning of the term "HMG-CoA reductase inhibitor" as used herein. Preferably, the HMG-CoA reductase inhibitor is selected from lovastatin and simvastatin, and most preferably simvastatin. Herein, the term "pharmaceutically acceptable salts" with respect to the HMG-CoA reductase inhibitor shall mean non toxic salts of the compounds employed in this invention which are generally prepared by reacting the free acid with a suitable organic or inorganic base, particularly those formed from cations such as sodium, potassium, aluminum, calcium, lithium, magnesium, zinc and tetramethylammonium, as well as those salts formed from amines such as ammonia, ethylenediamine, N-methylglucamine, lysine, arginine, ornithine, choline, N,N'-dibenzylethylenediamine, chloroprocaine, diethanolamine, procaine, N-benzylphenethylamine, 1-p-chlorobenzyl-2-pyrrolidine-1'-yl-methylbenz-imidazole, diethylamine, piperazine, and tris(hydroxymethyl)aminomethane. Further examples of salt forms of HMG-CoA reductase inhibitors may include, but are not limited to, acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexyl resorcinate, hydrabamine, hydrobromide, hydrochloride, hydroxynapthoate, iodide, isothionate, lactate, lactobionate, laurate, malate, maleate, mandelate, mesylate, methylsulfate, mucate, napsylate, nitrate, oleate, oxalate, pamaote, palmitate, panthothenate, phosphate/diphosphate, polygalacturonate, salicylate, stearate, subacetate, succinate, tannate, tartrate, teoclate, tosylate, triethiodide, and valerate.

Ester derivatives of the described HMG-CoA reductase inhibitor compounds may act as prodrugs which, when absorbed into the bloodstream of a warm-blooded animal, may cleave in such a manner as to release the drug form and permit the drug to afford improved therapeutic efficacy.

As used above, "integrin receptor antagonists" refers to compounds which selectively antagonize, inhibit or counteract binding of a physiological ligand to the alpha-v-beta-3 integrin, to compounds which selectively antagonize, inhibit or counteract binding of a physiological ligand to the alpha-v-beta-5 integrin, to compounds which antagonize, inhibit or counteract binding of a physiological ligand to both the alpha-v-beta-3 integrin and the alpha-v-beta-5 integrin, and to compounds which antagonize, inhibit or counteract the activity of the particular integrin(s) expressed on capillary endothelial cells. The term also refers to antagonists of the alpha-v-beta-6, alpha-v-beta-8, alpha-1-beta-1, alpha-2-beta-1, alpha-6-beta-1 and alpha-6-beta-4 integrins. The term also refers to antagonists of any combination of alpha-v-beta-3, alpha-v-beta-5, alpha-v-beta-6, alpha-v-beta-8, alpha-1-beta-1, alpha-2-beta-1, alpha-5-beta-1, alpha-6-beta-1 and alpha-6-beta-4 integrins. H. N. Lode and coworkers in PNAS USA 96: 1591-1596 (1999) have observed synergistic effects between an antiangiogenic alpha-v integrin antagonist and a tumor-specific antibody-cytokine (interleukin-2) fusion protein in the eradication of spontaneous tumor metastases. Their results suggested this combination as having potential for the treatment of cancer and metastatic tumor growth. Alpha-v-beta-3 integrin receptor antagonists inhibit bone resorption through a new mechanism distinct from that of all currently available drugs. Integrins are heterodimeric transmembrane adhesion receptors that mediate cell-cell and cell matrix interactions. The alpha-v-beta-3 integrin subunits interact non-covalently and bind extracellular matrix ligands in a divalent cation-dependent manner. The most abundant integrin on osteoclasts is alpha-v-beta-3 ($>10^7$/osteoclast), which appears to play a rate-limiting role in cytoskeletal organization important for cell migration and polarization. The alpha-v-beta-3 antagonizing effect is selected from inhibition of bone resorption, inhibition of restenosis, inhibition of macular degeneration, inhibition of arthritis, and inhibition of cancer and metastatic growth.

"An osteoblast anabolic agent" refers to agents that build bone, such as PTH. The intermittent administration of parathyroid hormone (PTH) or its amino-terminal fragments and analogues have been shown to prevent, arrest, partially reverse bone loss and stimulate bone formation in animals and humans. For a discussion refer to D. W. Dempster et al., "Anabolic actions of parathyroid hormone on bone," Endocr Rev 14: 690-709 (1993). Studies have demonstrated the clinical benefits of parathyroid hormone in stimulating bone formation and thereby increasing bone mass and strength. Results were reported by R M Neer et al., in New Eng J Med 344 1434-1441 (2001).

"A selective cyclooxygenase-2 inhibitor," or COX-2 inhibitor, refers to a type of nonsteroidal anti-inflammatory drug (NSAID), that inhibit the with the COX-2 coenzyme, which contributes to pain and inflammation in the body. Nonlimiting examples of COX-2 inhibitors include: celecoxib, etoricoxib, parecoxib, rofecoxib, lumaricoxib and valdecoxib.

In addition, parathyroid hormone-related protein fragments or analogues, such as PTHrP (1-36) have demonstrated potent anticalciuric effects; see M. A. Syed et al., "Parathyroid hormone-related protein-(1-36) stimulates renal tubular calcium reabsorption in normal human volunteers: implications for the pathogenesis of humoral hypercalcemia of malignancy," JCEM 86: 1525-1531 (2001) and may also have potential as anabolic agents for treating osteoporosis.

A preferred combination in accordance with the invention comprises co-dosing Form 2 crystalline polymorph simultaneously or sequentially with parathyroid hormone (PTH) or a fragment thereof, such as PTHrP (1-36).

In one embodiment, Form 2 crystalline polymorph and one or more pharmaceutically active agents are both administered orally. In another embodiment, Form 2 crystalline polymorph is administered orally and the one or more pharmaceutically active agents is/are administered via intravenous administration.

Those skilled in the art will recognise that the term treatment may also be extended to cover prophylaxis.

ABBREVIATIONS

IPA isopropylalcohol
IPAc isopropylacetate
DCM dichloromethane
TBME tert-butyl methyl ether
MEK methyl-ethyl-ketone (2-butanone)
MIBK methyl-isobutyl-ketone THF tetrahydrofuran
TFA trifluoroacetic acid
RH relative humidity
RT room temperature (typically 20° C.)
h hour
min minute

EXAMPLES

General Methods

X-Ray Powder Diffraction (XRPD)

XRPD diffractograms were collected either on a Bruker AXS C2 GADDS or a Bruker AXS D8 Advance diffractometer.

X-ray powder diffraction patterns on the Bruker AXS C2 GADDS diffractometer were acquired using Cu Kα radiation (40 kV, 40 mA), automated XYZ stage, laser video microscope for auto-sample positioning and a HiStar 2-dimensional area detector. X-ray optics consist of a single Göbel multilayer mirror coupled with a pinhole collimator of 0.3 mm.

The beam divergence, i.e. the effective size of the X-ray beam on the sample, was approximately 4 mm. A θ-θ continuous scan mode was employed with a sample-detector distance of 20 cm which gives an effective 2θ range of 3.2-29.7°. Typically the sample would be exposed to the X-ray beam for 120 seconds.

Samples run under ambient conditions were prepared as flat plate specimens using powder as received without grinding. Approximately 1-2 mg of the sample was lightly pressed on a glass slide to obtain a flat surface.

X-ray powder diffraction patterns on samples acquired on the Bruker AXS D8 Advance diffractometer were acquired using Cu Kα radiation (40 kV, 40 mA), θ-2θ goniometer, divergence of V4 and receiving slits, a Ge monochromator and a Lynxeye detector. The data were collected over an angular range of 2° to 42° 2θ using a step size of 0.05° 2θ and a collection time of 0.5 s/step.

Samples run under ambient conditions were prepared as flat plate specimens using powder as received. The sample was gently packed into a cavity cut into a polished zero-background (510) silicon wafer.

Samples run under ambient conditions were prepared as flat plate specimens using powder as received without grinding. Approximately 25-50 mg of the sample was gently packed into 12 mm diameter, 0.5 mm deep cavities cut into polished, zero-background (510) silicon wafers (The Gem Dugout, 1652 Princeton Drive, Pennsylvania State College, Pa. 16803, USA).

XRPD capillary studies were carried out using the High Resolution Bruker D8 diffractometer using the parameters described above. The data were processed using Diffrac Plus XRD Commander v2.6.1 software and visualised using Diffrac Plus EVA v 13.0.0.2 or v15.0.0.0 software. All samples (capillaries) were sealed and run at room temperature.

$^1$H NMR (Solution Phase)

Solution phase NMR spectra were collected on a Bruker 400 MHz instrument equipped with an auto-sampler and controlled by a DRX400 console. Automated experiments were acquired using ICON-NMR v4.0.7 running with Topspin v1.3 using the standard Bruker loaded experiments. For non-routine spectroscopy, data were acquired through the use of Topspin alone.

Samples were prepared in DMSO-$d_6$, unless otherwise stated. Off-line analysis was carried out using Topspin v1.3 or ACD SpecManager v12.5

$^{13}$C NMR (Solid State)

The analysis was carried out using a Varian VNMRS instrument operating at 100.56 MHz for $^{13}$C (399.88 MHz for 1H) and 376.24 MHz for $^{19}$F with a 4 mm (rotor o.d.) magic-angle spinning probe. Carbon-13 spectra were recorded from the sample using a crosspolarization magic-angle spinning (CPMAS) technique without and with dipolar dephasing (interrupted decoupling). Appropriate acquisition conditions were established using a set of short trial measurements: recycle 5 s, contact time 5 ms. A sample spin-rate of 10.0 kHz was used along with two-pulse phase-modulated (TPPM) 1H decoupling (at a radiofrequency field approximately equivalent to 75 kHz). The sample was run as-received and at ambient probe temperature (~30° C. at this spin rate). Spectra are referenced with respect to neat tetramethylsilane (by setting the high-frequency line from adamantane to 38.5 ppm). The $^{19}$F spectrum was obtained by direct excitation following a 3.6 μs 90° pulse, with a 60 s relaxation delay, at spin rate of 14 kHz and with no 1H decoupling. The spectrum is referenced relative to CFCl3.

The analysis was carried out using a Varian VNMRS instrument operating at 100.56 MHz for $^{13}$C (399.88 MHz for 1H) and a 6 mm (rotor o.d.) magic-angle spinning probe. Carbon-13 spectra were recorded from the sample using a cross-polarization magic-angle spinning (CPMAS) technique. Appropriate acquisition conditions were established using a set of short trial measurements: recycle 4 s, contact time 3 ms. A sample spin-rate of 6.8 kHz was used along with two-pulse phase-modulated (TPPM) $^1$H decoupling (at a radiofrequency field approximately equivalent to 54 kHz). The lower spin-rate used here compared to the previous measurements means that there are spinning sidebands in the spectra but these do not significantly interfere with the key centreband signals. Spectra are referenced with respect to neat tetramethylsilane (by setting the high-frequency line from adamantane to 38.5 ppm).

Thermodynamic Aqueous Solubility

Aqueous solubility was determined by suspending sufficient compound in water to give a maximum final concentration of ≥10 mg·ml$^{-1}$ of the parent free-form of the compound. The suspension was equilibrated at 25° C. for 24 hours then the pH was measured. The suspension was then filtered through a glass fibre C filter into a 96 well plate. The filtrate was then diluted by a factor of 101. Quantitation was by HPLC with reference to a standard solution of approximately 0.25 mg·ml$^{-1}$ in DMSO. Different volumes of the standard, diluted and undiluted sample solutions were injected. The solubility was calculated using the peak areas determined by integration of the peak found at the same retention time as the principal peak in the standard injection.

TABLE 1

HPLC method parameters for solubility measurements

| | | | |
|---|---|---|---|
| Type of method | Normal Phase | Reverse Phase | ✓ |
| | Isocratic | Gradient | ✓ |
| Test sample make-up: | DMSO | | |
| Column: | Phenomenex Gemini C18 50 × 4.6 mm 5 μM | | |
| Column Temperature (° C.): | 25 | | |
| Injection (μl): | 1, 2, 3, 5, 7, 10 | | |
| Detection: Wavelength, Bandwidth (nm): | 280 nm, 80 nm | | |
| Flow Rate (ml · min−1): | 2 | | |
| Phase A: | 0.1% TFA in water | | |
| Phase B: | 0.085% TFA in acetonitrile | | |

| | Time (min) | % Phase A | % Phase B |
|---|---|---|---|
| Timetable: | 0.0 | 95 | 5 |
| | 1.0 | 80 | 20 |
| | 2.3 | 5 | 95 |

TABLE 1-continued

HPLC method parameters for solubility measurements

| | | |
|---|---|---|
| 3.3 | 5 | 95 |
| 3.5 | 95 | 5 |
| 4.4 | 95 | 5 |

Analysis was performed on an Agilent HP1100 series system equipped with a diode array detector and using ChemStation software vB.02.01-SR1.

Differential Scanning Calorimetry (DSC)

DSC data were collected on a Mettler DSC 823e equipped with a 34 position auto-sampler. The instrument was calibrated for energy and temperature using certified indium. Typically 0.5-3 mg of each sample, in a pin-holed aluminium pan, was heated at 10° C./min from 25° C. to 300° C. A nitrogen purge at 50 ml/min was maintained over the sample.

The instrument control and data analysis software was STARe v9.20.

Thermogravimetric Analysis (TGA)

TGA data were collected on a Mettler TGA/SDTA 851e equipped with a 34 position auto-sampler. The instrument was temperature calibrated using certified indium. Typically 5-30 mg of each sample was loaded onto a pre-weighed aluminium crucible and was heated at 10° C./min from ambient temperature to 400° C. A nitrogen purge at 50 ml/min was maintained over the sample.

The instrument control and data analysis software was STARe v9.20.

Gravimetric Vapour Sorption (GVS)

Sorption isotherms were obtained using a SMS DVS Intrinsic moisture sorption analyser, controlled by DVS Intrinsic Control software v1.0.0.30. The sample temperature was maintained at 25° C. by the instrument controls. The humidity was controlled by mixing streams of dry and wet nitrogen, with a total flow rate of 200 ml/min The relative humidity was measured by a calibrated Rotronic probe (dynamic range of 1.0-100% RH), located near the sample. The weight change, (mass relaxation) of the sample as a function of % RH was constantly monitored by the microbalance (accuracy ±0.005 mg).

Typically 5-20 mg of sample was placed in a tared mesh stainless steel basket under ambient conditions. The sample was loaded and unloaded at 40% RH and 25° C. (typical room conditions). A moisture sorption isotherm was performed as outlined below (2 scans giving 1 complete cycle). The standard isotherm was performed at 25° C. at 10% RH intervals over a 0-90% RH range. Data analysis was undertaken in Microsoft Excel using DVS Analysis Suite v6.0.0.7.

TABLE 2

Method parameters for SMS DVS Intrinsic experiments

| Parameters | Values |
|---|---|
| Adsorption - Scan 1 | 40-90 |
| Desorption/Adsorption - Scan 2 | 90-0, 0-40 |
| Intervals (% RH) | 10 |
| Number of Scans | 2 |
| Flow rate (ml/min) | 200 |
| Temperature (° C.) | 25 |
| Stability (° C./min) | 0.2 |
| Sorption Time (hours) | 6 hour time out |

The sample was recovered after completion of the isotherm and re-analysed by XRPD.

Example 1

Synthesis of N-[1-6-(ethynyl-3-oxo-hexahydro-furo[3,2-b]pyrrole-4-carbonyl)-3-methyl-butyl]-4-[5-fluoro-2-(4-methyl-piperazin-1-yl)thiazol-4-yl]-benzamide Free Base (Compound I Free Base)

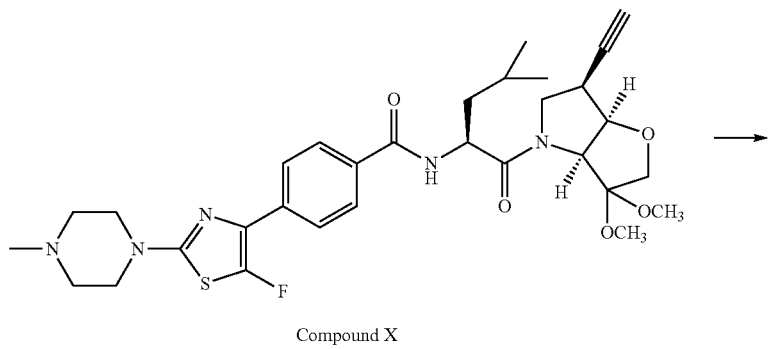

Compound X

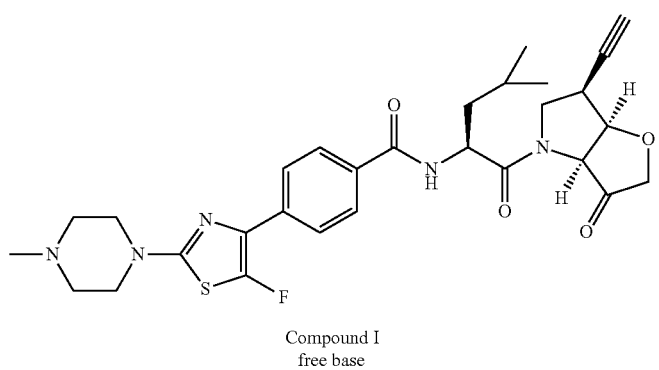

Compound I
free base

Compound X was prepared as described in WO2010/034788 Example 2.

A solution of Compound X (89.6 g, 146 mmol) was concentrated in vacuo at 50° C. to give 100 g of oil. The oil was dissolved in toluene (250 mL), and solvent removed by distillation in vacuo at 50-55° C. This was repeated once more. The residue was dissolved in methylene chloride (70 mL).

A 3 L, 3-necked, round-bottomed reactor was charged with trifluoroacetic acid (800 mL), and cooled to −5±2° C. The reactor was evacuated to less than 100 mBar, and the vacuum released with nitrogen. A solution of Compound X in methylene chloride was added to the cooled trifluoroacetic acid over 10 minutes while keeping the temperature at −5±2° C. The addition funnel was rinsed with methylene chloride (20 mL). Cooling was removed, and the reaction temperature was allowed to reach ambient temperature. The reaction was stirred for 16 h at ambient temperature, at which point in-process control by HPLC showed >99.0% conversion.

Toluene (900 mL) and heptanes (900 mL) were added, and stirred for 1-3 minutes. The phases were allowed to separate. The lower phase, containing the trifluoroacetic acid salt of Compound I, was retained, whilst the upper phase was discarded. The lower phase was stirred with toluene (900 mL) and heptanes (900 mL) for 5 minutes. The phases were allowed to separate. The upper phase was discarded. The lower phase was diluted with methylene chloride (700 mL). A 6 L, 3-necked, round-bottomed reactor was charged with 20% $K_2HPO_4$ (aq. potassium phosphate, dibasic) (4 L) and methylene chloride (700 mL). This mixture was cooled to 0° C., and the methylene chloride solution of the trifluoroacetic acid salt of Compound I was added to the quench mixture, while keeping the temperature at 2-10° C. The phases were allowed to separate, and the organic phase was retained. The aqueous phase was extracted with methylene chloride (2×700 mL).

The combined organic phases were successively washed with 10% $K_2HPO_4$ (aq. potassium phosphate, dibasic) (2×500 mL). The combined organic phases were heated to 35° C. and dried with magnesium sulphate (50 g) for 20 minutes at 35° C. The suspension was filtered and the filter cake was washed with methylene chloride (35° C., 500 mL). The filtrate was concentrated in vacuo to dryness at 35-45° C. The evaporation residue was dissolved in methylene chloride (100 mL). TBME (300 mL) was added dropwise. The product started to crystallize on standing. The mixture was concentrated in vacuo at 35° C. until 150 mL of distillate had been collected. At this point, a thin suspension was obtained. Additional TBME (450 mL) was added dropwise, resulting in a yellow suspension. The suspension was cooled to 5° C., and stirred at this temperature for 16 h. The suspension was filtered, and the filter cake was washed with TBME (200 mL). The filter cake was dried in vacuo at 30° C. for 6 h to give 55.3 g (65%) of Compound I free base. The HPLC purity is 96.8%.

As discussed above, Compound I free base may also exist in the hydrate form.

An amorphous form of the free base may be converted to a crystalline form of the free base by a process involving slurrying it in 3 vol 98:2 IPA:water at 50° C. for 1 h.

The XRPD diffractogram of a sample of crystalline Compound I free base is shown in FIG. 3.

Example 2

Preparation of Various Salt Forms of Compound I Free Base

Attempts were made to prepare various salt forms of Compound I free base. In order to do so, it was decided to utilise two solvent systems: one with nominally dry solvent and one with an excess of water added. Following consideration of the properties of Compound I, IPAc was chosen as the dry solvent based and MIBK was chosen as the second solvent.

Experimental Procedure

Into each of 36 4 mL glass vials was accurately weighed ca. 30 mg of Compound I free base. To half of these vials was added 3.0 mL of IPAc and to the other half was added 3 mL MIBK and 30 µL of deionised water. To each of the vials was then added an acid shown in Table 3:

TABLE 3

Acids used in experiment to form salts

| | | | | IPAc (A) | | MIBK + 1% water (B) | |
|---|---|---|---|---|---|---|---|
| | | Details | | | | | |
| Index | Acid | Added as | Stochiometry | Mass API (mg) | Amount acid added | Mass API (mg) | Amount acid added |
| 1 | Hydrochloric acid | 1M solution in THF | mono | 29.0 | 51 µL | 28.6 | 50 µL |
| 2 | Sulphuric acid | 1M solution in THF | mono | 34.4 | 61 µL | 31.7 | 56 µL |
| 3 | Sulphuric acid | 1M solution in THF | hemi | 28.6 | 25 µL | 30.4 | 27 µL |
| 4 | Tosic acid | 1M solution in EtOH | mono | 29.1 | 51 µL | 31.0 | 55 µL |
| 5 | Methanesulphonic acid | 1M solution in THF | mono | 29.6 | 52 µL | 31.6 | 56 µL |
| 6 | L-aspartic acid | solid | mono | 30.9 | 7 mg | 29.3 | 7 mg |
| 7 | L-aspartic acid | solid | hemi | 28.4 | 4 mg | 30.0 | 3 mg |
| 8 | Maleic acid | 1M solution in THF | mono | 29.0 | 51 µL | 31.3 | 55 µL |
| 9 | Phosphoric acid | 1M solution in THF | mono | 25.8 | 45 µL | 34.7 | 61 µL |
| 10 | L-tartaric acid | 1M solution in THF | mono | 26.0 | 46 µL | 28.0 | 49 µL |
| 11 | fumaric acid | 0.5M solution in 1:1 THF:MeOH | mono | 29.5 | 104 µL | 31.0 | 109 µL |
| 12 | citric acid | 1M solution in THF | mono | 28.1 | 50 µL | 32.4 | 57 µL |
| 13 | D-glucuronic acid | solid | mono | 26.8 | 9 mg | 31.7 | 11 mg |
| 14 | L-Malic acid | 1M solution in THF | mono | 32.5 | 57 µL | 33.6 | 59 µL |
| 15 | L-Lactic acid | 1M solution in THF | mono | 31.0 | 55 µL | 29.8 | 53 µL |
| 16 | L-ascorbic acid | 1M solution in water | mono | 26.5 | 47 µL | 29.4 | 52 µL |
| 17 | Succinic acid | 1M solution in THF | mono | 31.4 | 55 µL | 27.2 | 48 µL |
| 18 | Acetic acid | 1M solution in THF | mono | 35.2 | 62 µL | 30.6 | 54 µL |

The IPAc experiments were then incubated between ambient and 50° C. (switching between each temperature every 4 hours), whilst the MIBK experiments were incubated at RT. After 24 h, the vials were inspected and the appearances noted. Many of the MIBK experiments had formed gums, so these vials were transferred to the ambient/50° C. incubator.

Vials were inspected again after a further 24 h and appearances noted. Solids obtained were filtered off and analysed by XRPD. Any vials not containing solids at this point were uncapped and allowed to evaporate, with any resulting solid being analysed by XRPD.

Results

Results are summarized in Tables 4 and 5 below. The IPAc experiments produced a total of twelve isolated solids; three of these were identified as the input acids, one was a partially crystalline HCl salt and eight were amorphous solids.

Only four solids were isolated from the MIBK experiments; two input acids and two brown amorphous solids.

TABLE 4

Salt screening experiments performed in IPAc

| | Details | | | 24 h | | 48 h | | Isolated solid | |
|---|---|---|---|---|---|---|---|---|---|
| Index | Acid | Stochiometry | Observations | | Actions | Observations | Actions | Description | XRPD |
| 1A | Hydrochloric acid | mono | Cloudy suspension, some gum | | none | Cloudy suspension, some gum | filtered | off white powder | partially crystalline |
| 2A | Sulphuric acid | mono | fine suspension | | none | fine suspension | filtered | off white powder | amorphous |
| 3A | Sulphuric acid | hemi | fine suspension | | none | fine suspension | filtered | off white powder | amorphous |
| 4A | Tosic acid | mono | gum | | none | gum | slow evap | n/a | n/a |
| 5A | Methanesulphonic acid | mono | clumpy suspension | | none | clumpy suspension | filtered | off white powder | amorphous |
| 6A | L-aspartic acid | mono | small amount of solid in a clear solution | | none | small amount of solid in a clear solution | filtered | off white powder | input acid |
| 7A | L-aspartic acid | hemi | small amount of solid in a clear solution | | none | small amount of solid in a clear solution | filtered | off white powder | input acid |
| 8A | Maleic acid | mono | gummy solid, clear solution | | none | gummy solid, clear solution | filtered | orange/brown powder | amorphous |
| 9A | Phosphoric acid | mono | fine suspension | | none | fine suspension | filtered | off white powder | amorphous |
| 10A | L-tartaric acid | mono | fine suspension | | none | fine suspension | filtered | off white powder | amorphous |
| 11A | fumaric acid | mono | clear solution | | none | small amount of solid | slow evap | n/a | n/a |
| 12A | citric acid | mono | clumpy suspension | | none | clumpy suspension | filtered | off white powder | amorphous |
| 13A | D-glucuronic acid | mono | clumpy suspension | | none | clumpy suspension | filtered | off white powder | input acid |
| 14A | L-Malic acid | mono | gummy solid, clear solution | | none | gummy solid, clear solution | filtered | orange/brown powder | amorphous |
| 15A | L-Lactic acid | mono | small amount of solid in a clear solution | | none | small amount of solid in a clear solution | slow evap | n/a | n/a |
| 16A | L-ascorbic acid | mono | gum | | none | gum | slow evap | n/a | n/a |
| 17A | Succinic acid | mono | clear solution | | none | clear solution | slow evap | n/a | n/a |
| 18A | Acetic acid | mono | small amount of solid in a clear solution | | none | small amount of solid in a clear solution | slow evap | n/a | n/a |

TABLE 5

Salt screening experiments performed in MIBK + 1% water

| | Details | | | 24 h | | 48 h | | Isolated solid | |
|---|---|---|---|---|---|---|---|---|---|
| Index | Acid | Stochiometry | Observations | | Actions | Observations | Actions | Description | Form |
| 1B | Hydrochloric acid | mono | gum | | Moved to 25/50° C. | gum | slow evap | n/a | n/a |
| 2B | Sulphuric acid | mono | gum | | Moved to 25/50° C. | gum | slow evap | n/a | n/a |
| 3B | Sulphuric acid | hemi | gum | | Moved to 25/50° C. | gum | slow evap | n/a | n/a |
| 4B | Tosic acid | mono | gum | | Moved to 25/50° C. | gum | slow evap | n/a | n/a |

TABLE 5-continued

Salt screening experiments performed in MIBK + 1% water

| Index | Acid | Stochiometry | 24 h Observations | 24 h Actions | 48 h Observations | 48 h Actions | Isolated solid Description | Isolated solid Form |
|---|---|---|---|---|---|---|---|---|
| 5B | Methanesulphonic acid | mono | gum | Moved to 25/50° C. | gum | slow evap | n/a | n/a |
| 6B | L-aspartic acid | mono | small amount of solid in a clear solution | Moved to 25/50° C. | small amount of solid in a clear solution | slow evap | off white solid | input acid |
| 7B | L-aspartic acid | hemi | small amount of solid in a clear solution | Moved to 25/50° C. | small amount of solid in a clear solution | slow evap | off white solid | input acid |
| 8B | Maleic acid | mono | gum | Moved to 25/50° C. | gum | slow evap | n/a | n/a |
| 9B | Phosphoric acid | mono | gum | Moved to 25/50° C. | gum | slow evap | n/a | n/a |
| 10B | L-tartaric acid | mono | gum | Moved to 25/50° C. | gum | slow evap | n/a | n/a |
| 11B | fumaric acid | mono | clear solution | Moved to 25/50° C. | clear solution | slow evap | n/a | n/a |
| 12B | citric acid | mono | gum | Moved to 25/50° C. | gum | slow evap | n/a | n/a |
| 13B | D-glucuronic acid | mono | gum | Moved to 25/50° C. | gum | slow evap | n/a | n/a |
| 14B | L-Malic acid | mono | gum | Moved to 25/50° C. | gum | slow evap | n/a | n/a |
| 15B | L-Lactic acid | mono | some gum, some solid | Moved to 25/50° C. | some gum, some solid | slow evap | n/a | n/a |
| 16B | L-ascorbic acid | mono | oil | Moved to 25/50° C. | oil | slow evap | n/a | n/a |
| 17B | Succinic acid | mono | small amount of solid in a clear solution | Moved to 25/50° C. | small amount of solid in a clear solution | filtered | brown powder | amorphous |
| 18B | Acetic acid | mono | small amount of solid in a clear solution | Moved to 25/50° C. | small amount of solid in a clear solution | filtered | brown powder | amorphous |

All samples that had evaporated and failed to give any solid were taken up in 500 μL of MEK and 5 μL water added. The vials were then incubated between ambient and 50° C. for two days after which time there was still no solid present in any of the samples. Vials were uncapped and to allowed to evaporate, all giving brown gums.

Example 3

Further Investigation of Sulfate and Mesylate Salt Forms of Compound I Free Base Into each of two 10 mL glass vials was weighed ca. 100 mg of Compound I free base. 10.0 mL of IPAc was then added to each followed by 1 eq of either sulphuric acid (as a 1M solution in THF) or methanesulphonic acid (as a 1M solution in THF). In both cases a fluffy white precipitate was evolved upon addition of the acid. Vials were incubated between ambient and 50° C. for 72 h, cycling every four hours. Solids were then filtered off and air dried.

Roughly 10 mg of the amorphous sulphate salt was weighed into each of six vials and the same was done with the mesylate salt. To each vial was added 100 μL of the relevant solvent shown in Table 6. The vials were then incubated between ambient and 50° C. overnight with any solids then filtered off and analysed by XRPD.

TABLE 6

Conditions for maturation of amorphous sulphate and mesylate salts

| Details | | Sulphuric Acid (A) | | Methanesulphonic acid (B) | |
|---|---|---|---|---|---|
| Index | Solvent | Observations | XRPD | Observations | XRPD |
| ADC704-43-1 | MeCN | gummy solid | n/a | solution | n/a |
| ADC704-43-2 | THF | gum/oil | n/a | gum/oil | n/a |
| ADC704-43-3 | 1,4-dioxane | suspension | crystalline | gum/oil | n/a |
| ADC704-43-4 | MEK | gum | n/a | gum/oil | n/a |
| ADC704-43-5 | TBME | clumpy solid | amorphous | clumpy solid | amorphous |
| ADC704-43-6 | EtOAc | gum | n/a | gum | n/a |

Whilst the solids isolated from TBME were both amorphous, the sulphate salt maturated in 1,4-dioxane showed a new crystalline diffraction pattern. TGA analysis of the crystalline material produced by this process revealed it to be a crystalline dioxane solvate and therefore of limited utility.

Based on the results of Examples 2 and 3, the hydrochloride salt was taken forward for further investigation.

Example 4

Synthesis of Form 2 Crystalline Polymorph from Compound I Free Base

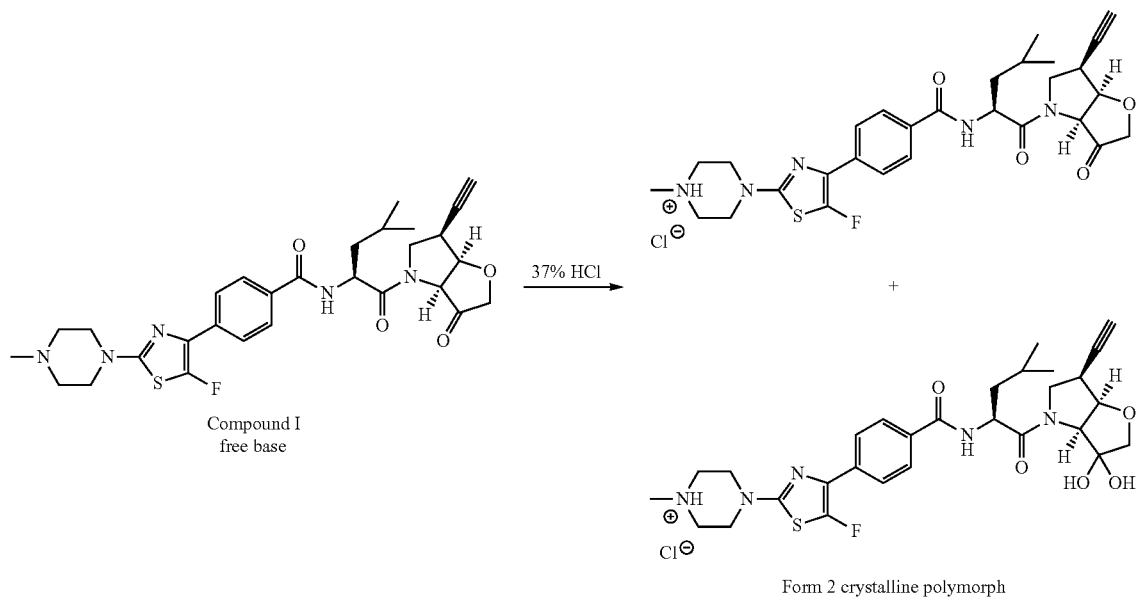 [SMILES: C#C[C@@H]1CN(C(=O)[C@H](CC(C)C)NC(=O)c2ccc(-c3nc(N4CCN(C)CC4)sc3F)cc2)[C@@H]2C(=O)CO[C@H]12 ; C#C[C@@H]1CN(C(=O)[C@H](CC(C)C)NC(=O)c2ccc(-c3nc(N4CC[NH+](C)CC4)sc3F)cc2)[C@H]2[C@@H]1OCC2(O)O ; C#C[C@@H]1CN(C(=O)[C@H](CC(C)C)NC(=O)c2ccc(-c3nc(N4CC[NH+](C)CC4)sc3F)cc2)[C@@H]2C(=O)CO[C@H]12 ; [Cl-] ; [Cl-]]

Compound I free base

Form 2 crystalline polymorph

Compound I free base (99.2 mg) was weighed into a reaction tube and acetone (2.0 mL) added, giving a clear solution after brief stirring. 37% HCl (14 µL, as a solution in 1.0 mL acetone) was then added and the resulting clear solution stirred at 50° C. for 1 h, after which time a white precipitate had formed. The reaction tube was cooled to 20° C. at 0.1° C./minute and then stirred at 20° C. for a further 8 hours. The solid present was isolated by filtration and dried under vacuum at 60° C. overnight to give 65 mg (61%) of off white solid. The product was determined to be Form 2 crystalline polymorph.

Example 5

Synthesis of Form 2 Crystalline Polymorph from Compound I Free Base (Alternative Method Involving Antisolvent and Seeding)

A 1 L, 3-necked, round-bottomed reactor was evacuated to less than 100 mBar and the vacuum was released with nitrogen. The reactor was then charged with acetone (164 mL, 128.9 g) and Compound I free base (70 mmol; 41 g). The suspension was heated on a water bath to 50° C. and stirred at this temperature until a clear solution of Compound I free base was obtained. Concentrated hydrochloric acid (37%) (6.90 g, 70 mmol, 1.0 eq.) was added over 3 min. The clear solution was stirred for 1 min. followed by seeding with Form 2 crystalline polymorph (~20 mg). Precipitation started immediately but was allowed to "mature" by stirring the suspension at 50° C. for 30 min. Tert-butyl methyl ether (410 mL, 303.8 g) was added at 48±2° C. over 19 min. The suspension was then cooled to 22° C. over 2 h and stirred at this temperature for 2 h, before cooling to 12° C. and stirring at 12° C. for 20 min. The suspension was filtered, and the filter cake was washed with acetone/tert-butyl methyl ether (1:2) (120 mL), followed by tert-butyl methyl ether (120 mL). The filter cake was dried in vacuo at 50° C. for 64 h to give 42.09 g (96%) of Form 2 crystalline polymorph. The HPLC purity was 97.4%.

Material produced using this process was used for the testing described in Examples 11 and 12. Similar experiments were performed using IPA and THF as solvent and the results are shown in Table 7.

TABLE 7

| Solvent | Yield | HPLC purity | Crystalline form (XRPD) |
|---------|-------|-------------|-------------------------|
| IPA     | 75%   | 98.5%       | Form 2 crystalline polymorph |
| THF     | 96%   | 97.1%       | Form 2 crystalline polymorph |

Example 6

Synthesis of Form 2 Crystalline Polymorph from Compound I Free Base (Further Alternative Method Involving Seeding)

Compound I free base (1.696 g) was weighed into a reaction tube and acetone (10.0 mL) was added. The reaction tube was heated to 50° C. with magnetic stirring, resulting in a clear solution. The solution was then seeded with Form 2 crystalline polymorph (10 mg). A solution of 37% HCl (237 µL) was then made up in acetone (10.0 mL). This acid solution was then added in 2.5 mL portions to the reaction tube. After stirring at 50° C. for 1 h, the resulting fine suspension was cooled to 5° C. at 0.1° C./min and stirred at this temperature for 48 h. The solid present was then isolated by filtration and washed with acetone that had been cooled to 0° C. (2×10 mL). This solid was then dried under vacuum at 60° C. for 24 h prior to characterisation to give title product (1.51 g, 83%) as an off white powder. The XRPD diffractogram of a sample of this material was obtained as described in Example 9 and is shown in FIG. 1.

Material from this process was used for the testing described in Examples 13, 14 and 15.

Reference Example 7

Synthesis of N-[1-6-(ethynyl-3-oxo-hexahydro-furo [3,2-b]pyrrole-4-carbonyl)-3-methyl-butyl]-4-[5-fluoro-2-(4-methyl-piperazin-1-yl)thiazol-4-yl]-benzamide monohydrochloride—Amorphous Form An amorphous form of N-[1-6-(ethynyl-3-oxo-hexahydro-furo[3,2-b]pyrrole-4-carbonyl)-3-methyl-butyl]-4-[5-fluoro-2-(4-methyl-piperazin-1-yl)thiazol-4-yl]-benzamide monohydrochloride was prepared in the following experiment:

Compound I free base (502 mg) was dissolved in isopropyl acetate (10 mL) to give a clear golden solution. The solution was treated with 4M HCl in dioxane (214 μl, 1.0 Eq) which induced immediate precipitation of a fine white solid. The solid was concentrated in vacuo to yield a fine off-white powder which was dried. XRPD analysis showed that the material was amorphous (data not shown). As for the free base, the monohydrohloride salt may also exist in the hydrate form. However, the ratio of ketone:hydrate in the amorphous form was not determined.

Reference Example 8

Synthesis of N-[1-6-(ethynyl-3-oxo-hexahydro-furo [3,2-b]pyrrole-4-carbonyl)-3-methyl-butyl]-4-[5-fluoro-2-(4-methyl-piperazin-1-yl)thiazol-4-yl]-benzamide monohydrochloride—Form 1 Crystalline Polymorph A crystalline form of N-[1-6-(ethynyl-3-oxo-hexahydro-furo[3,2-b]pyrrole-4-carbonyl)-3-methyl-butyl]-4-[5-fluoro-2-(4-methyl-piperazin-1-yl)thiazol-4-yl]-benzamide monohydrochloride with a different XRPD diffractogram to Form 2 crystalline polymorph—named Form 1 crystalline polymorph—was prepared in the following experiment:

200 mg Compound I free base was dissolved in THF and 3 eq HCl (37% HCl made up in 1 vol THF) was added at 50° C. After 1 h standing at 50° C., 70 μL water was added and the solution cooled to ambient temperature. A crystalline solid resulted which upon isolation by filtration was dried under vacuum at 50° C. The ratio of ketone:hydrate in the Form 11 polymorph was not determined. The XRPD diffractogram of a sample of this material is shown in FIG. 2.

An alternative method for preparing Form 1 crystalline polymorph of N-[1-6-(ethynyl-3-oxo-hexahydro-furo[3,2-b] pyrrole-4-carbonyl)-3-methyl-butyl]-4-[5-fluoro-2-(4-methyl-piperazin-1-yl)thiazol-4-yl]-benzamide monohydrochloride involves cooling a 50° C. solution in 4 volumes of THF with 1% water (v/v) to 20° C. at 0.1° C./min.

Example 9

XRPD Analysis of Compound I Free Base, Form 2 Crystalline Polymorph and Form 1 Crystalline Polymorph XRPD analysis of crystalline Compound I free base and Form I and Form II crystalline polymorphs was undertaken using the method describe in General Methods. The results are shown in FIGS. 1, 2 and 3 and Tables 8-10 below. All materials are crystalline as shown by the XRPD diffractograms.

TABLE 8 peak listing corresponding to FIG. 1
(a sample of Form 2 crystalline polymorph)

| Angle (2-Theta °) | Rel. Intensity |
|---|---|
| 6.8 | 54.0 |
| 8.9 | 14.7 |
| 11.7 | 43.0 |
| 12.1 | 57.8 |
| 12.4 | 34.3 |
| 13.5 | 59.5 |
| 14.9 | 68.7 |
| 15.5 | 33.7 |
| 16.7 | 39.9 |
| 17.0 | 28.9 |
| 17.8 | 100.0 |
| 19.0 | 70.1 |
| 19.5 | 38.8 |
| 20.3 | 25.5 |
| 21.2 | 39.3 |
| 21.5 | 28.5 |
| 22.1 | 13.2 |
| 23.3 | 25.0 |
| 23.9 | 49.4 |
| 24.1 | 96.5 |
| 24.6 | 49.0 |
| 24.8 | 71.1 |
| 25.5 | 32.5 |
| 26.0 | 13.3 |
| 26.6 | 33.3 |
| 27.2 | 19.3 |
| 28.2 | 14.1 |
| 29.1 | 20.9 |
| 29.6 | 19.0 |
| 29.9 | 10.1 |
| 30.3 | 9.1 |
| 31.5 | 11.6 |
| 32.1 | 16.5 |

TABLE 9 peak listing corresponding to FIG. 2
(a sample of Form 1 crystalline polymorph)

| Angle (2-Theta °) | Rel. Intensity |
|---|---|
| 3.9 | 69.3 |
| 7.5 | 19.7 |
| 9.2 | 100.0 |
| 11.8 | 20.5 |
| 13.1 | 10.9 |
| 14.6 | 32.3 |
| 15.3 | 13.0 |
| 15.7 | 29.7 |
| 18.4 | 20.4 |
| 18.9 | 12.0 |
| 19.2 | 14.8 |
| 19.7 | 15.8 |
| 20.1 | 21.3 |
| 21.0 | 15.8 |
| 22.0 | 6.9 |
| 22.6 | 7.5 |
| 23.1 | 7.3 |
| 23.6 | 8.1 |
| 25.2 | 41.1 |
| 25.4 | 30.8 |
| 26.3 | 12.0 |
| 26.8 | 8.6 |
| 29.3 | 12.1 |

TABLE 10 peak listing corresponding to FIG. 3
(a sample of crystalline Compound I free base)

| Angle (2-Theta °) | Rel. Intensity |
|---|---|
| 4.0 | 100.0 |
| 8.0 | 19.9 |
| 11.3 | 13.9 |
| 12.0 | 34.9 |
| 13.5 | 22.3 |
| 13.9 | 12.4 |
| 14.4 | 5.0 |
| 15.3 | 7.7 |
| 16.0 | 9.3 |
| 17.4 | 18.9 |
| 18.0 | 15.8 |
| 18.2 | 17.2 |
| 18.7 | 30.2 |
| 19.6 | 14.4 |
| 20.2 | 20.4 |
| 20.4 | 30.9 |
| 20.8 | 34.1 |
| 21.6 | 10.7 |
| 22.7 | 43.1 |
| 23.1 | 8.2 |
| 23.4 | 7.9 |
| 24.0 | 6.7 |
| 25.3 | 27.6 |
| 26.0 | 9.0 |
| 26.5 | 7.4 |

Example 10

Figure 4:
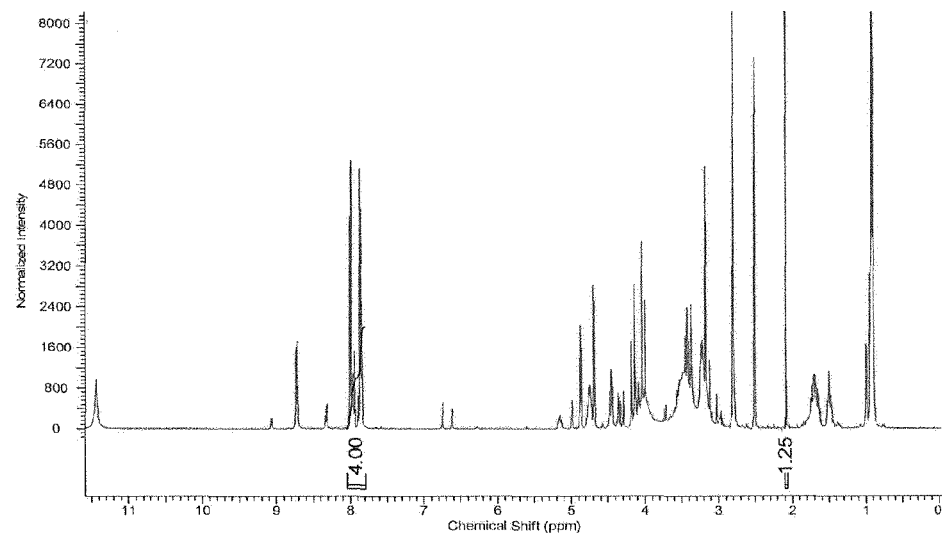
FIG. 4 shows the $^1$H NMR spectrum of a sample of Form 2 crystalline polymorph dissolved in DMSO solution.

Solution Phase $^1$H NMR Analysis of a Sample of Form 2 Crystalline Polymorph $^1$H NMR analysis of Form 2 crystalline polymorph was carried out using the method described in General Methods. The resulting spectrum is shown in FIG. 4, from which it is evident that the sample of Form 2 crystalline polymorph exists in ketone-hydrate equilibrium.

Example 11

Figure 5:
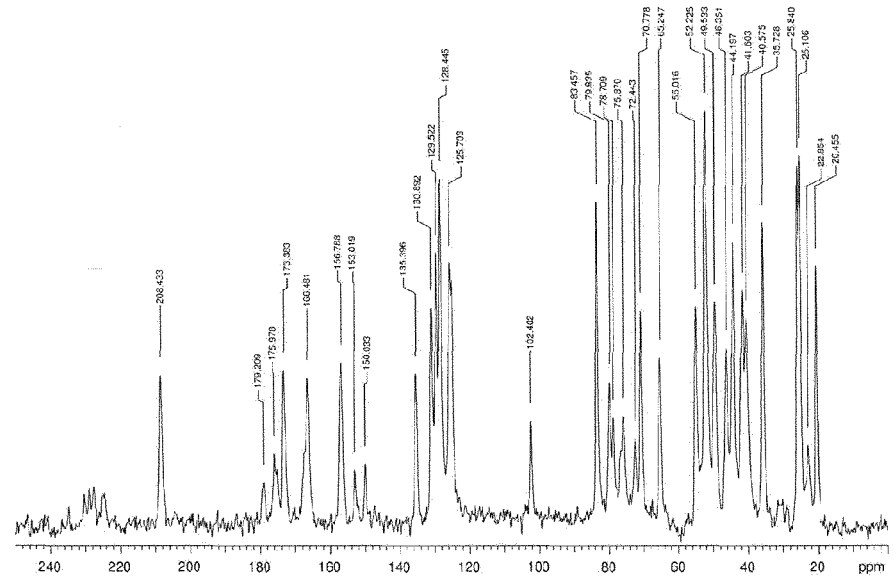
FIG. 5 shows the solid state $^{13}$C NMR spectrum of a sample of Form 2 crystalline polymorph.

Solid State $^{13}$C NMR Structural Analysis of Form 2 Crystalline Polymorph The $^{13}$C solid state NMR spectrum of a sample of Form 2 crystalline polymorph produced using the method of Example 5 is illustrated in FIG. 5. Based on the integration of the 208 ppm (ketone) and 102 ppm (hydrate) signals, the ketone:hydrate ratio was determined to be 67:33.

Environmental Dependence of Spectra

Figure 6:
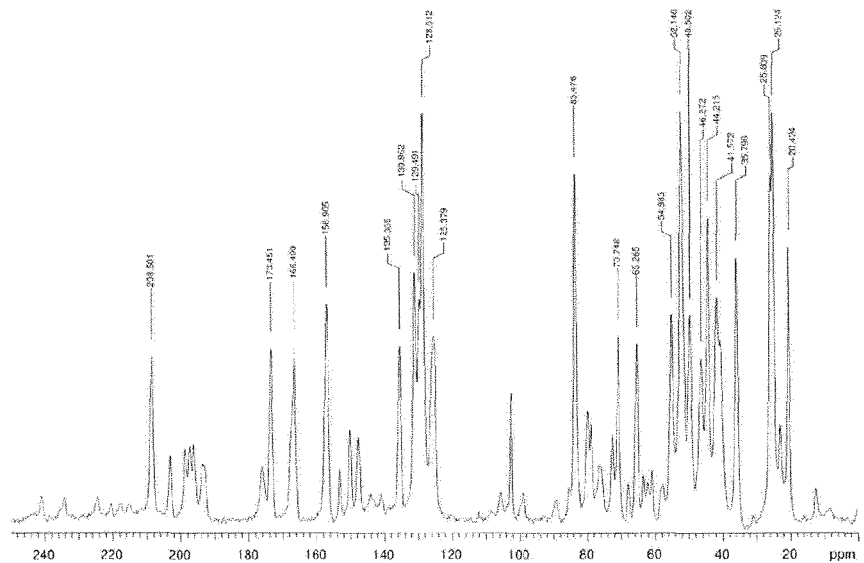
FIG. 6 shows the solid state $^{13}$C NMR spectrum of a sample of Form 2 crystalline polymorph, after being stored for 1 week at <2% RH.
Figure 7:
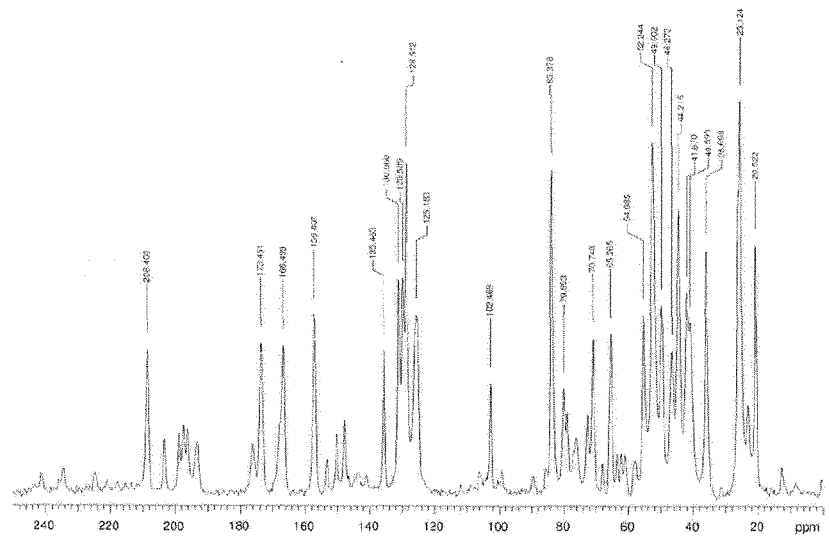
FIG. 7 shows the solid state $^{13}$C NMR spectrum of a sample of Form 2 crystalline polymorph, after being stored for 1 week at 75% RH.
Figure 8:
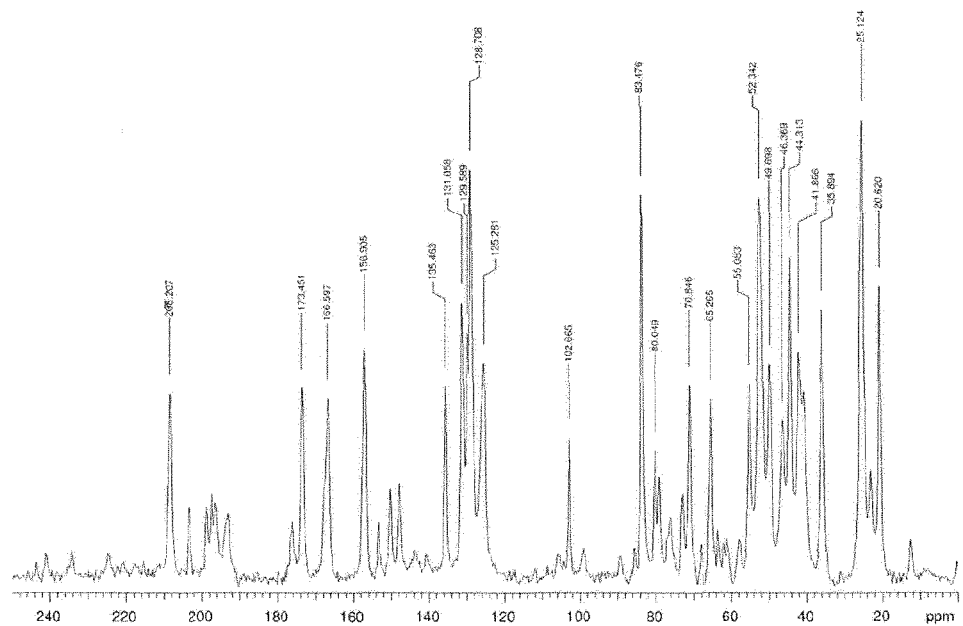
FIG. 8 shows the solid state $^{13}$C NMR spectrum of a sample of Form 2 crystalline polymorph, after being stored for 1 week at 80% RH.

The $^{13}$C solid state NMR spectrum illustrated in FIG. 6 was recorded after the sample had been stored at a relative humidity of <2% for one week. Of the total intensity in the ketone/hydrate signals the ketone accounts for 67% of this (i.e. ketone:hydrate ratio of 67:33). The $^{13}$C solid state NMR spectrum shown in FIG. 7 was recorded after the sample had been stored at 75% RH for one week. The ketone accounts for 67% of the signal. The $^{13}$C solid state NMR spectrum shown in FIG. 8 was recorded at 80° C. and gives a ketone content of 68%. As such, it can be seen that the ratio of ketone to hydrate did not change under different environmental conditions.

Relaxation Dependence of Spectra

In general, if a sample is a mixture of components then it should be possible to vary the NMR acquisition conditions to favour one or other of those components. This will be successful as long as the relaxation behaviour is different for each component. The $^1$H spin-lattice relaxation time ($T_1$(H)) can be used as the basis for one such "filter", and the $^1$H spin-lattice relaxation in the rotating frame time ($T_{1\rho}$(H)) as the basis for another. The latter tends to be the most sensitive to differences between components.

Figure 9:
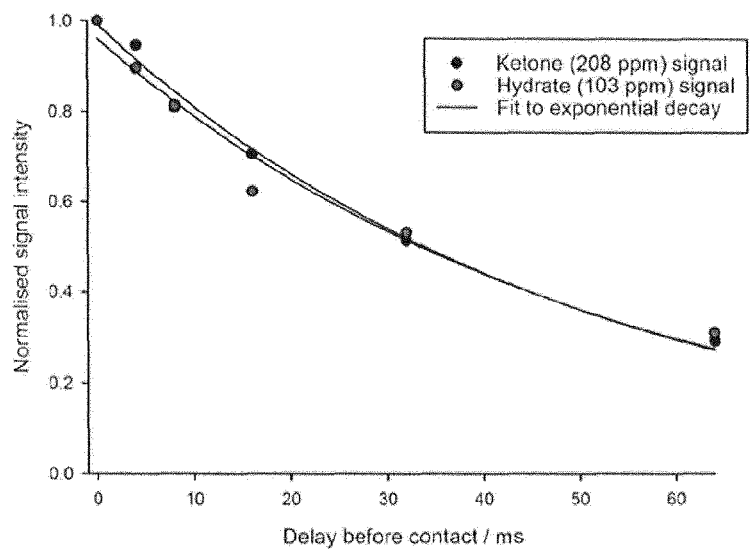
FIG. 9 shows the results of an NMR experiment performed on a sample of Form 2 crystalline polymorph examining the relaxation behaviour of diagnostic ketone and hydrate $^{13}$C NMR signals.

A delayed contact CP experiment was used to look for differences associated with the diagnostic ketone (208 ppm) and hydrate (103 ppm) signals. The result is shown in FIG. 9.

To within experimental error the behaviour of both signals was the same. There was, therefore, no evidence that the ketone and hydrate components were in different phases (although given the similarity in the rest of the molecule in the two forms it could not be ruled out that the relaxation behaviour was coincidentally the same).

Figure 10:
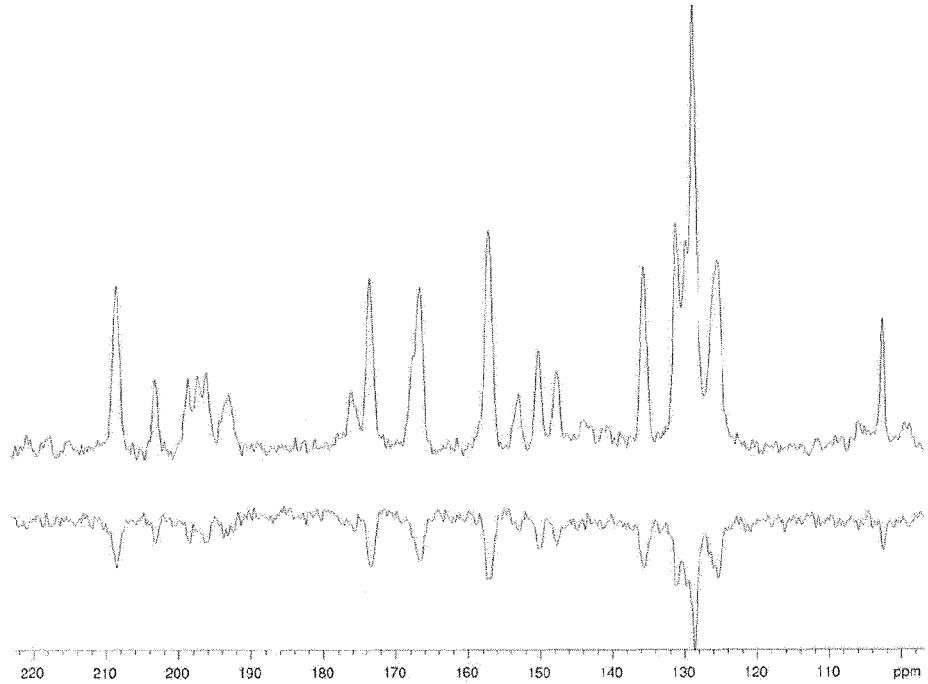
FIG. 10 show the results of a further NMR experiment performed on a sample of Form 2 crystalline polymorph to identify differences between the diagnostic ketone and hydrate signals.

If the $T_{1\rho}$ behaviour is indistinguishable it is unlikely that the $T_1$ would show any differences. Nevertheless, a short series of measurements was carried out to check this. FIG. 10 shows the results from an inversion recovery CP measurement showing the full signal at the top and that from an attempt to null the signal below it. Again, there is no evidence for any difference in the behaviour of the ketone and hydrate signals.

Hence, it may be concluded that the ketone and hydrate forms are in the same phase in the crystal.

Example 12

Capillary XRPD Structural Analysis of Form 2 Crystalline Polymorph

Figure 11:
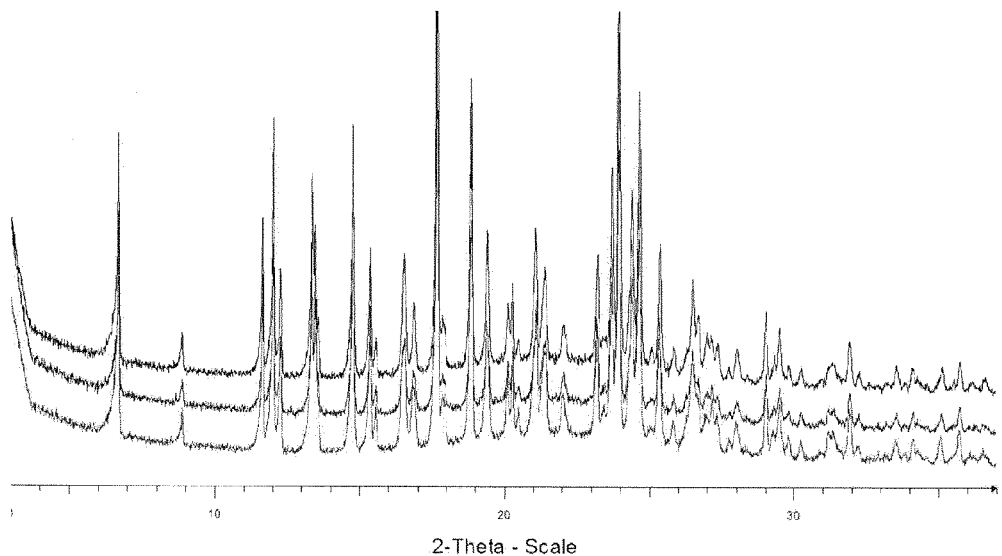
FIG. 11 shows capillary X-ray powder diffraction patterns of samples from three batches of Form 2 crystalline polymorph.

Following the methods set out above in General Procedures, capillary XRPD data was obtained for three batches of Form 2 crystalline polymorph. The superimposed diffractograms are illustrated in FIG. 11, where it can be seen the three sets of data were identical, indicating consistency and reproducibility between batches.

The data from the three batches was indexed in order to determine the unit cell parameters of the crystalline material. The Pawley fitting results are summarized in Table 11.

TABLE 11

| Batch No. | Unit cell parameters (a, b, c in Å) | Volume Å$^3$ | Pawley fit |
|---|---|---|---|
| 1 | 7.49/15.33/26.24 | 3017.3 | 2.65 |
| 2 | 7.49/15.31/26.25 | 3013.9 | 1.73 |
| 3 | 7.49/15.30/26.25 | 3009.3 | 1.46 |

The results confirm that the three powder data sets are related to the same crystalline structure as they display the same pattern. Overall, the Pawley fit values were observed to be in good agreement between calculated and observed profiles, with Batch No. 3 showing the best results. The subtle differences observed mainly in Batch No. 1 can be related to a series of artifacts which can be attributed to: structural defects, disordered configuration of one of the chemical entities, dislocations in the crystallites.

The crystal system of Form 2 crystalline polymorph was found to be orthorhombic (multiplicity X4) and it was determined that one molecule and one chloride ion can be accommodated in the asymmetric unit cell (740 Å$^3$).

Based on the solid state NMR indicating a ratio of from about 1:1 to about 4:1, for example 2:1 of ketone to hydrate, either:

both chemical entities crystallise interchangeably in the same phase in a ratio of from about 1:1 to about 4:1, for example 2:1; or a co-crystal exists with both chemical entities crystallised in a regular repeating pattern in the same phase a conglomerate exists with a ratio of about 1:1 to about 4:1, for example 2:1 of ketone crystals to hydrate crystals.

The latter option is not consistent with the results of Example 11 and Example 12 which concluded that the ketone and hydrate forms are in the same phase, whilst the second option is not possible when only one molecule is known to be in the asymmetric unit, therefore it may be concluded that both chemical entities crystallise interchangeably in the same phase in a ratio of from about 1:1 to about 4:1, for example 2:1.

Example 13

Thermodynamic Aqueous Solubility of Compound I Free Base and Form 2 Crystalline Polymorph Thermodynamic aqueous solubility of Compound I free base and Form 2 crystalline polymorph was determined using the method described in General Methods. The results are shown in Table 12 below:

TABLE 12

| Form | Aqueous solubility |
|---|---|
| Free base (amorphous) | 0.3 mg/mL at pH 5.8 |
| HCl (Form 2 crystalline polymorph) | 82 mg/mL at pH 3.5 |
| HCl (Form 1 crystalline polymorph) | 19 mg/mL at pH 4.0 |

These results show that Form 2 crystalline polymorph had very high water solubility, as compared with the poor solubility for Compound I free base even in amorphous form and the comparatively poor solubility of the Form 1 crystalline polymorph.

Example 14

Figure 12:
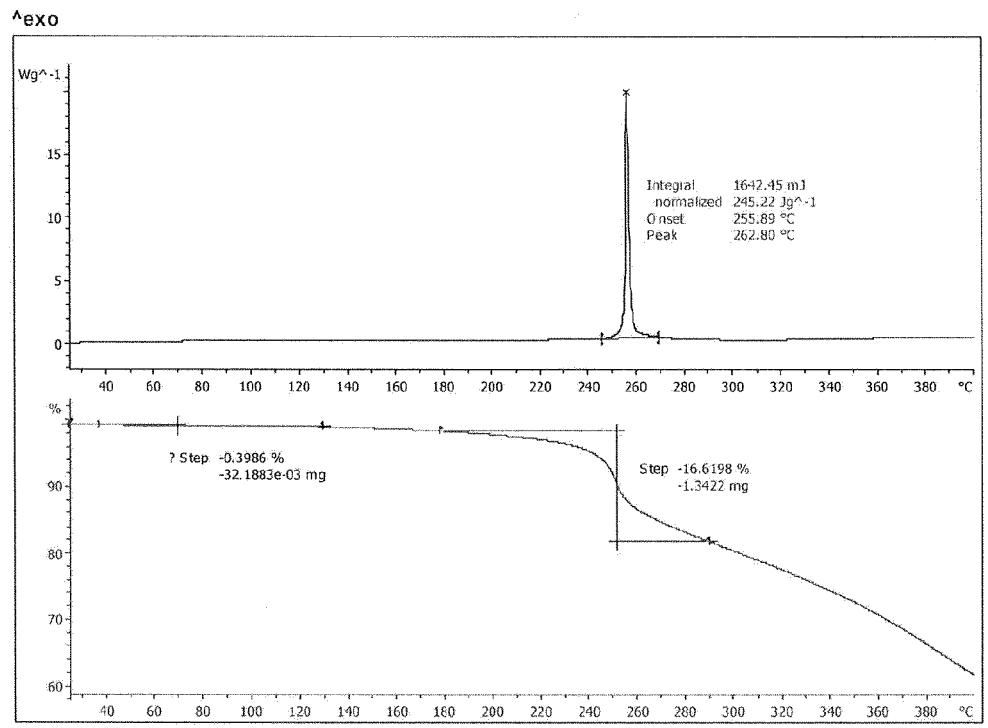
FIG. 12 shows thermal analysis of a sample of Form 2 crystalline polymorph (upper graph is DSC and lower graph is TGA).
Figure 13:
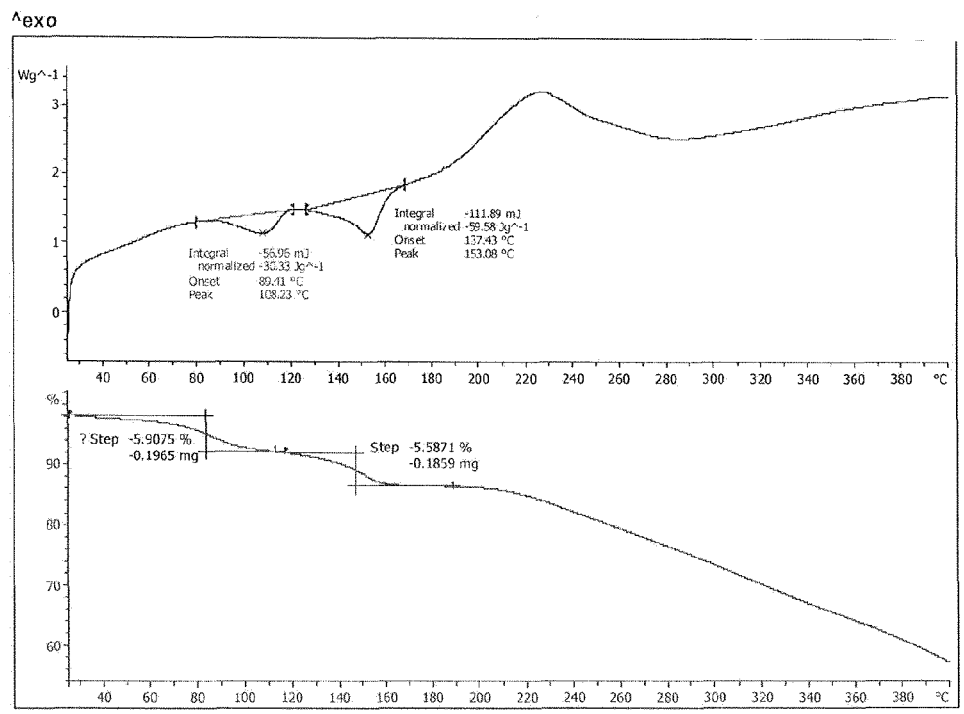
FIG. 13 shows thermal analysis of a sample of Form 1 crystalline polymorph (upper graph is DSC and lower graph is TGA).
Figure 14:
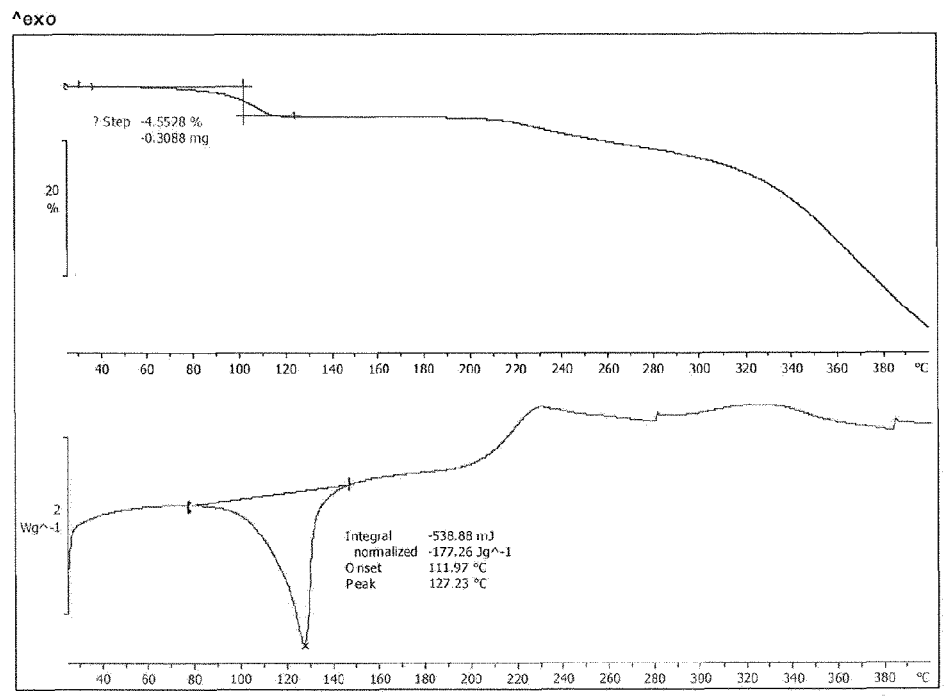
FIG. 14 shows thermal analysis of a sample of crystalline Compound I free base (upper graph is DSC and lower graph is TGA).

Thermal Analysis of Compound I Free Base, Form 2 Crystalline Polymorph and Form 1 Crystalline Polymorph Thermal analysis of Form 2 crystalline polymorph (a sample obtained using the method in Example 6) by DSC and TGA was undertaken using the method describe in General Methods. From FIG. 12 upper graph it can be seen that the substance has good thermal stability, with a small mass loss until degradation begins at 160° C. This is clearly superior to Form 1 crystalline polymorph (FIG. 13) which shows two distinct mass losses below 160° C. and also superior to the crystalline Compound I free base (FIG. 14) which shows a mass loss (probably water) at a temperature below 110° C. indicating that these two forms would be far more difficult to handle.

Example 15

Gravimetric Vapour Sorption of Form 2 Crystalline Polymorph

Figure 15:
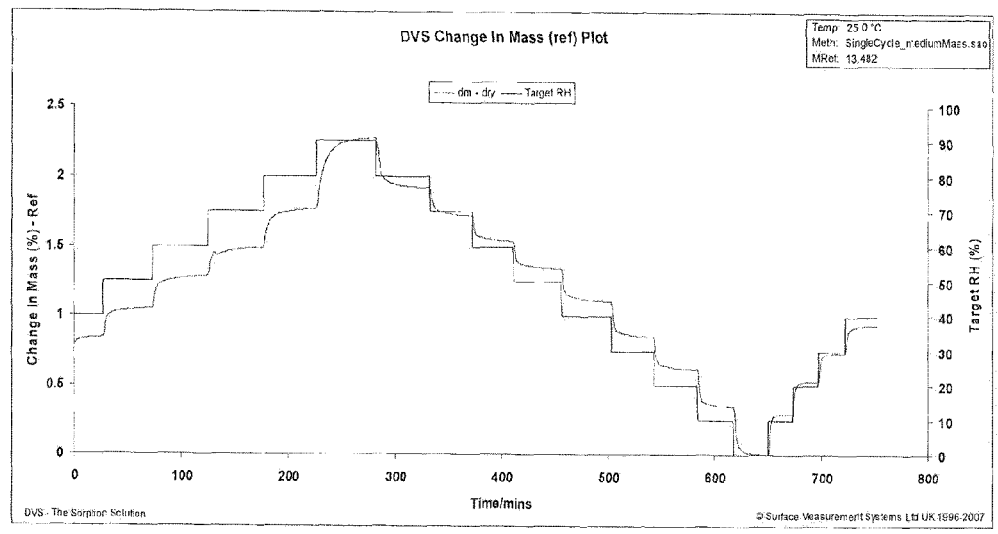
FIG. 15 shows gravimetric vapour sorption analysis (DVS change in mass plot) of a sample of Form 2 crystalline polymorph.
Figure 16:
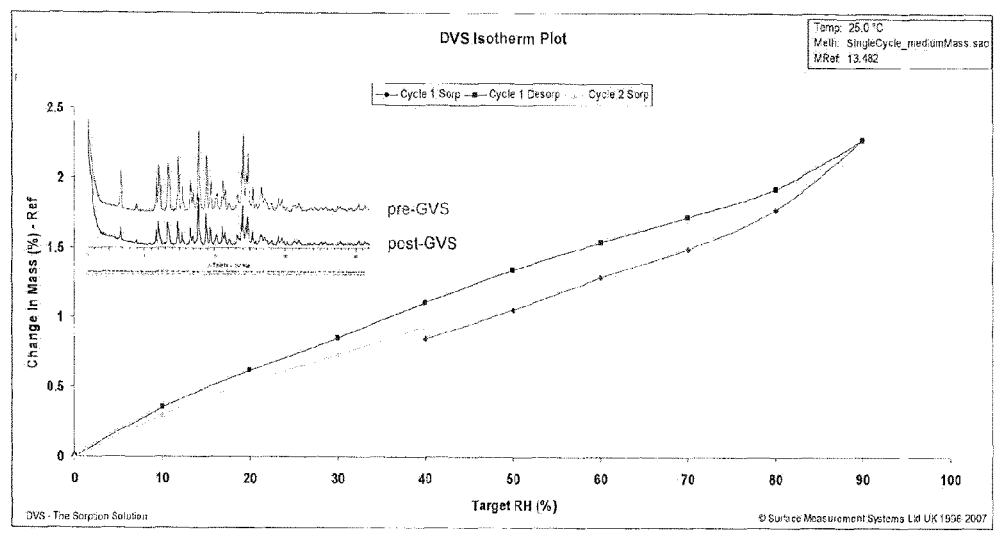
FIG. 16 shows gravimetric vapour sorption analysis (DVS isotherm plot) of a sample of the Form 2 crystalline polymorph.

Gravimetric vapour sorption analysis of Form 2 crystalline polymorph (a sample obtained using the method in Example 6) was undertaken using the method described in General Methods. Results are shown in FIGS. 15 and 16. These figures show that the substance takes up ca 2.2% water over the 0-90% RH range and that this water uptake is reversible. As such the substance does not appear to be at risk of humidity mediated form change and that it seems that it can be handled over a wide RH range.

Example 16

Large Scale Synthesis of N-[1-6-(ethynyl-3-oxo-hexahydro-furo[3,2-b]pyrrole-4-carbonyl)-3-methyl-butyl]-4-[5-fluoro-2-(4-methyl-piperazin-1-yl)thiazol-4-yl]-benzamide Free Base (Compound I Free Base)

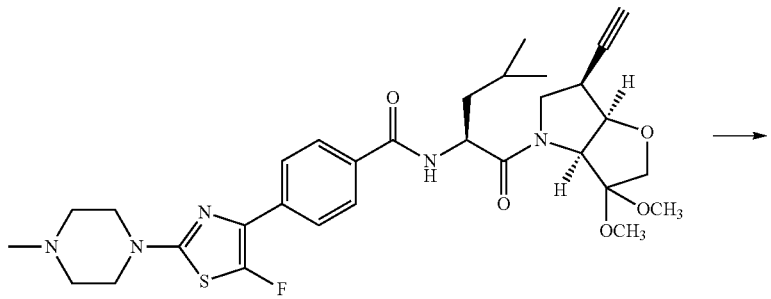

Compound X

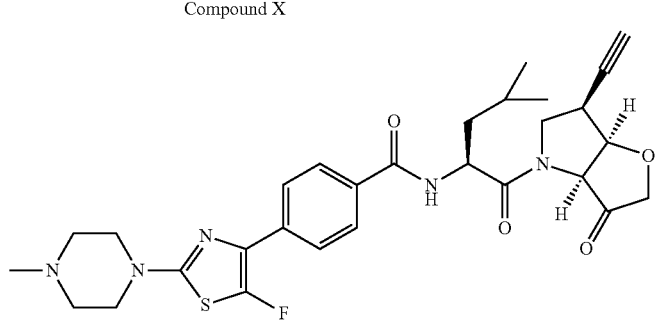

Compound I
free base

Compound X was prepared as described in WO2010/034788 Example 2.

A solution of Compound X (9.500 kg, 15.5 mol) was transferred to a reactor and the solvents removed by distillation at reduced pressure. Toluene (2×23.0 kg) was added and removed in vacuo at reduced pressure. The evaporation residue was dissolved in dichloromethane (17 kg) and the resulting solution was added to a mixture of trifluoroacetic acid (70.8 kg) and purified water (0.500 kg) at 10° C. The resulting mixture was heated to 22° C. and stirred at this temperature until a conversion (HPLC) of 99.5% of Compound X to Compound I free base was obtained. The reaction mixture was then added to a mixture of n-heptane (97.0 kg) and tert-butyl methyl ether (105.6 kg) at 0° C. After stirring at 0° C., the material was isolated by filtration and washed with a mixture of n-heptane (38.6 kg) and tert-butyl methyl ether (38.6 kg).

The wet material was dissolved in dichloromethane (204.0 kg) and washed with 20% aqueous $K_2HPO_4$ at pH 7.5. The organic phase was cooled to 15° C. and applied to a column prepared from silica gel 60 (40-63 μM) (55.5 kg) methylene chloride (202.7 kg) and acetone (13.4 kg). The column was eluted with: 1) 20% v/v acetone (35.0 kg) in tert-butyl methyl ether (132.0 kg), 2) 50% v/v acetone (131.5 kg) in tert-butyl methyl ether (124.0 kg) and 3) acetone (875.0 kg). The eluent fractions containing the desired product (determined using TLC and HPLC) were evaporated to a volume of ca. 90 L. tert-Butyl methyl ether (64.5 kg) and purified water (1.585 kg) were then added and distillation continued. When a volume of ca. 50 L was reached, tert-butyl methyl ether (32.0 kg) and purified water (1.635 kg) were added. The suspension was cooled to 2° C. and stirred at this temperature. The product was isolated by filtration, washed with tert-butyl methyl ether (27.0 kg) and dried under vacuum at 30° C. for at least 10 hours to give 6.5 kg (72%) of Compound I free base.

Example 17

Large Scale Synthesis of Form 2 Crystalline Polymorph from Compound I Free Base

Compound I free base (6.325 kg, 10.8 mol) was added to a mixture of acetone (25.50 kg) and TBME (2.40 kg). 37% Hydrochloric acid (0.960 kg, 9.74 mol) was added and the suspension heated as quickly as possible to 50° C. to obtain a clear solution. The solution was seeded with Form 2 crystalline polymorph (12 g) and stirred at 50° C. Precipitation of the Form 2 crystalline polymorph was observed. Further precipitation was induced by addition at 50° C. of: 1) 50% v/v acetone (10.25 kg) in TBME (9.75 kg) and then 2) TBME (65.0 kg). The resulting suspension was cooled as quickly as possible to 10° C. and after stirring for 20 min at this temperature the product was filtered off, washed first with 29% v/v acetone (4.50 kg) in TBME (10.25 kg) and then with TBME (14.50 kg). The product was dried under vacuum at 50° C. for at least 20 hours to give 6.0 kg (89%) of Form 2 crystalline polymorph.

The XRPD diffractogram of a sample of this material is shown in FIG. 17. $^1H$ NMR analysis (not shown; 500 MHz Bruker machine, DMSO d6, temperature 298° C., NOESY, 1d/zg30 signal pulse) indicated that the ratio of ketone to hydrate is 82:18.

SUMMARY OF THE RESULTS DISCLOSED IN THE EXAMPLES

Form 2 crystalline polymorph exists as a single crystalline phase consisting of both N-[1-6-(ethynyl-3-oxo-hexahydro-furo[3,2-b]pyrrole-4-carbonyl)-3-methyl-butyl]-4-[5-fluoro-2-(4-methyl-piperazin-1-yl)thiazol-4-yl]-benzamide monohydrochloride and N-[1-6-(ethynyl-3-oxo-hexahydro-furo[3,2-b]pyrrole-4-carbonyl)-3-methyl-butyl]-4-[5-fluoro-2-(4-methyl-piperazin-1-yl)thiazol-4-yl]-benzamide hydrate monohydrochloride.

Surprisingly, the ketone and hydrate forms were not observed to interconvert on exposure to conditions of varying relative humidity, indicating that the ratio of ketone to hydrate form is stable.

Form 2 crystalline polymorph has good water solubility and good moisture and thermal stability.

Form 2 crystalline polymorph is clearly advantageous over Form 1 crystalline polymorph and over the free base

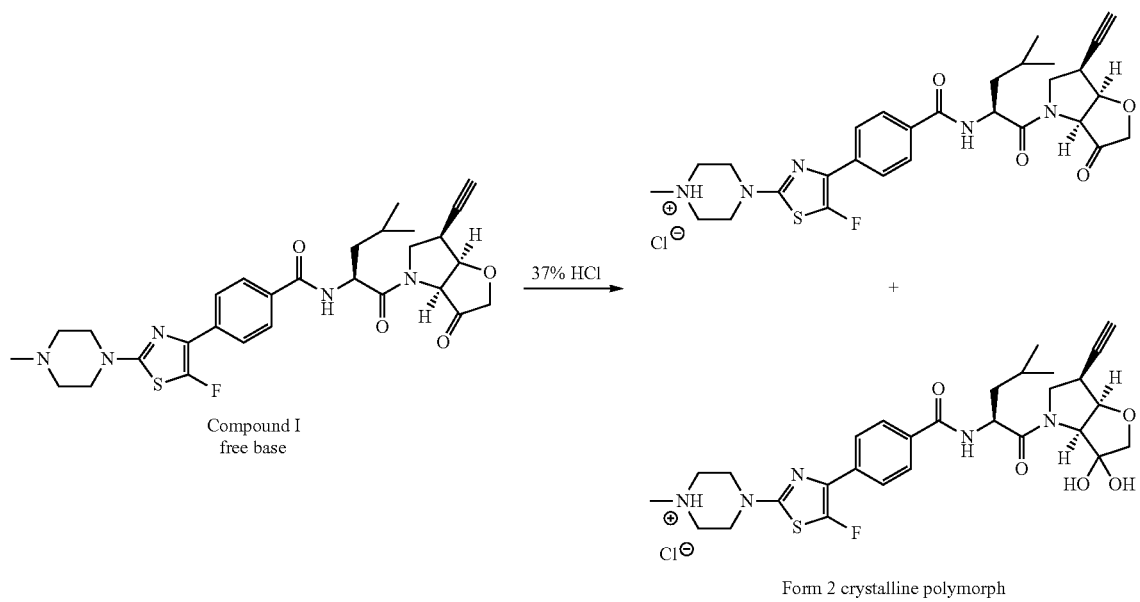 [SMILES: C#C[C@@H]1CN(C(=O)[C@H](CC(C)C)NC(=O)c2ccc(-c3nc(N4CCN(C)CC4)sc3F)cc2)[C@@H]2C(=O)CO[C@H]12 ; C#C[C@@H]1CN(C(=O)[C@H](CC(C)C)NC(=O)c2ccc(-c3nc(N4CC[NH+](C)CC4)sc3F)cc2)[C@H]2[C@@H]1OCC2(O)O ; C#C[C@@H]1CN(C(=O)[C@H](CC(C)C)NC(=O)c2ccc(-c3nc(N4CC[NH+](C)CC4)sc3F)cc2)[C@@H]2C(=O)CO[C@H]12 ; [Cl-] ; [Cl-]]

form of Compound I, even when in crystalline form, in terms of water solubility and thermal stability.

Attempts to make crystalline forms of other salts of Compound I free base were generally unsuccessful.

Large scale processes (Examples 16 and 17) produced Compound I free base and Form 2 crystalline polymorph in good yield and purity, thereby confirming that the methodology for forming the compounds is robust.

All references referred to in this application, including patent and patent applications, are incorporated herein by reference to the fullest extent possible.

Throughout the specification and the claims which follow, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps.

The application of which this description and claims forms part may be used as a basis for priority in respect of any subsequent application. The claims of such subsequent application may be directed to any feature or combination of features described herein. They may take the form of product, composition, process, or use claims and may include, by way of example and without limitation, the following claims:

The invention claimed is:

1. Form 2 crystalline polymorph consisting of a mixture of N-[1-6-(ethynyl-3-oxo-hexahydro-furo[3,2-b]pyrrole-4-carbonyl-3-methyl-butyl]-4-[5-fluoro-2-(4-methyl-piperazin-1-yl)thiazol-4-yl]-benzamide monohydrochloride and N-[1-6-(ethynyl-3-oxo-hexahydro-furo[3,2-b]pyrrole-4-carbonyl)-3-methyl-butyl]-4-[5-fluoro-2-(4-methyl-piperazin-1-yl)thiazol-4-yl]-benzamide hydrate monohydrochloride, wherein the mixture exists as a single crystalline phase.

2. A pharmaceutical composition comprising Form 2 crystalline polymorph according to claim 1 and one or more pharmaceutically acceptable diluents or carriers.

3. A pharmaceutical combination comprising Form 2 crystalline polymorph according to claim 1 together with a further pharmaceutically active agent useful in the treatment of osteoporosis, glucocorticoid induced osteoporosis, Paget's disease, abnormally increased bone turnover, periodontal disease, gingival disease, tooth loss, bone fractures, atherosclerosis, rheumatoid arthritis, osteoarthritis, periprosthetic osteolysis, osteogenesis imperfecta, metastatic bone disease, and hypercalcemia of malignancy.

4. A method for the treatment of a disorder mediated by cathepsin K comprising administering a safe and effective amount of Form 2 crystalline polymorph according to claim 1.

5. A method according to claim 4, characterised in that the disorder is osteoporosis.

6. A method according to claim 4, characterised in that the disorder is osteoarthritis.

7. A method according to claim 4, characterised in that the Form 2 crystalline polymorph is administered in combination with one or more further pharmaceutically active agents useful for the treatment of osteoporosis and osteoarthritis.

8. A method according to claim 7, wherein the further one or more pharmaceutically active agent is selected from an organic bisphosphonate; an estrogen receptor modulator; an androgen receptor modulator; an inhibitor of osteoclast proton ATPase; an inhibitor of HMG-CoA reductase; an integrin receptor antagonist; Vitamin B D or an analogue thereof, an osteoblast anabolic agent; a selective cyclooxygenase-2 inhibitor (COX-2 inhibitor); an inhibitor of interleukin-1-beta; a LOX/COX inhibitor, a RANKL inhibitor; an anti-sclerostin antibody and pharmaceutically acceptable salts and mixtures thereof.

9. A method according to claim 7 or claim 8, characterised in that the Form 2 crystalline polymorph and one or more pharmaceutically active agents are all administered orally.

10. A method according to claim 7 or claim 8, characterised in that the Form 2 crystalline polymorph is administered orally and the one or more further pharmaceutically active agents are administered via intravenous administration.

11. A method for the preparation of Form 2 crystalline polymorph according to claim 1 comprising reacting N-[1-6-(ethynyl-3-oxo-hexahydro-furo[3,2-b]pyrrole-4-carbonyl)-3-methyl-butyl]-4-[5-fluoro-2-(4-methyl-piperazin-1-yl)thiazol-4-yl]-benzamide free base with hydrochloric acid in the presence of a solvent selected from acetone, IPA, IPAc EtOAc, THF and MEK and crystallising the Form 2 crystalline polymorph from the said solvent.

12. A method according to claim 11, wherein the solvent is acetone.

13. A method according to claim 11 or claim 12 wherein the crystallising is performed under conditions of slow cooling or temperature cycling.

14. A method according to claim 11, wherein the crystallising is performed in the presence of a seed amount of Form 2 crystalline polymorph consisting of a mixture of N-[1-6-(ethynyl-3-oxo-hexahydro-furo[3,2-b]pyrrole-4-carbonyl-3-methyl-butyl]-4-[5-fluoro-2-(4-methyl-piperazin-1-yl)thiazol-4-yl]-benzamide monohydrochloride and N-[1-6-(ethynyl-3-oxo-hexahydro-furo[3,2-b]pyrrole-4-carbonyl)-3-methyl-butyl]-4-[5-fluoro-2-(4-methyl-piperazin-1-yl) thiazol-4-yl]-benzamide hydrate monohydrochloride, wherein the mixture exists as a single crystalline phase.

15. A method according claim 11 wherein the crystallising is promoted by use of an antisolvent selected from acetone and TBME.

16. The method according to claim 15, wherein the antisolvent is TBME.

17. A method for the preparation of Form 2 crystalline polymorph according to claim 1 comprising:
(i) reacting N-[1-6-(ethynyl-3-oxo-hexahydro-furo[3,2-b] pyrrole-4-carbonyl)-3-methyl-butyl]-4-[5-fluoro-2-(4-methyl-piperazin-1-yl)thiazol-4-yl]-benzamide free base with hydrochloric acid in the presence of acetone and TBME;
(ii) seeding the solution with Form 2 crystalline polymorph; and
(iii) inducing crystallization by the addition of acetone and TBME.

18. Form 2 crystalline polymorph obtainable by a method according to claim 11 or claim 17.

19. A method for the preparation of a pharmaceutical composition according to claim 2 comprising bringing Form 2 crystalline polymorph into association with one or more pharmaceutically acceptable diluents or carriers.

20. Material consisting of a mixture of N-[1-6-(ethynyl-3-oxo-hexahydro-furo[3,2-b]pyrrole-4-carbonyl)-3-methyl-butyl]-4-[5-fluoro-2-(4-methyl-piperazin-1-yl)thiazol-4-yl]-benzamide monohydrochloride and N-[1-6-(ethynyl-3-oxo-hexahydro-furo[3,2-b]pyrrole-4-carbonyl)-3-methyl-butyl]-4-[5-fluoro-2-(4-methyl-piperazin-1-yl)thiazol-4-yl]-benzamide hydrate monohydrochloride in the form of its Form 2 crystalline polymorph, wherein the mixture exists as a single crystalline phase and having an XRPD pattern substantially as shown in FIG. 1.

21. Material consisting of a mixture of N-[1-6-(ethynyl-3-oxo-hexahydro-furo[3,2-b]pyrrole-4-carbonyl)-3-methylbutyl]-4-[5-fluoro-2-(4-methyl-piperazin-1-yl)thiazol-4-yl]-benzamide monohydrochloride and N-[1-6-(ethynyl-3-oxo-hexahydro-furo[3,2-b]pyrrole-4-carbonyl)-3-methyl-butyl]-4-[5-fluoro-2-(4-methyl-piperazin-1-yl)thiazol-4-yl]-benzamide hydrate monohydrochloride in the form of its Form 2 crystalline polymorph, wherein the mixture exists as a single crystalline phase and having an XRPD pattern containing three, four, five, six, seven, eight, nine, ten, eleven or all twelve peaks selected from 6.8, 12.4, 14.9, 16.7, 17.0, 17.8, 24.1, 24.6, 24.8, 27.2, 28.2, 32.1 (+0.2 degrees, 2-theta values).

22. Material according to claim 21 having an XRPD pattern containing three, four, five, six, seven or all eight peaks selected from 6.8, 12.4, 14.9, 16.7, 17.8, 24.1, 24.6 and 24.8 (±0.2 degrees, 2-theta values).

23. Material according to claim 22 having an XRPD pattern containing three, four, five or all six peaks selected from 6.8, 14.9, 17.8, 24.1, 24.6 and 24.8 (±0.2 degrees, 2-theta values).

24. A method according to claim 8, wherein the osteoblast anabolic agent is PTH.

* * * * *